(12) United States Patent
Kitagawa et al.

(10) Patent No.: US 9,829,486 B2
(45) Date of Patent: Nov. 28, 2017

(54) SENSOR DEVICE

(71) Applicant: PANASONIC CORPORATION, Osaka (JP)

(72) Inventors: Yusuke Kitagawa, Kyoto (JP); Kiyoshi Hashimotodani, Kyoto (JP); Susumu Fukushima, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 109 days.

(21) Appl. No.: 14/369,940

(22) PCT Filed: Feb. 20, 2013

(86) PCT No.: PCT/JP2013/000924
§ 371 (c)(1),
(2) Date: Jun. 30, 2014

(87) PCT Pub. No.: WO2013/132761
PCT Pub. Date: Sep. 12, 2013

(65) Prior Publication Data
US 2014/0370584 A1    Dec. 18, 2014

(30) Foreign Application Priority Data
Mar. 5, 2012    (JP) ................. 2012-047628

(51) Int. Cl.
*G01N 33/543* (2006.01)
*G01N 21/41* (2006.01)
(Continued)

(52) U.S. Cl.
CPC .. *G01N 33/54373* (2013.01); *B01L 3/502761* (2013.01); *G01N 21/03* (2013.01);
(Continued)

(58) Field of Classification Search
CPC .. G01N 33/54373; G01N 21/41; G01N 21/03; G01N 21/05; G01N 21/77
(Continued)

(56) References Cited

U.S. PATENT DOCUMENTS 5,626,134 A * 5/1997 Zuckerman ........ A61B 5/14555
356/41
6,670,115 B1 * 12/2003 Zhang ................ G01N 33/5438
204/193
(Continued)

FOREIGN PATENT DOCUMENTS

CN           1379857 A      11/2002
JP       2005-181296 A       7/2005
(Continued)

OTHER PUBLICATIONS

International Search Report issued in International Application No. PCT/JP2013/00924 dated Mar. 26, 2013, with English Translation.
(Continued)

*Primary Examiner* — Jill Warden
*Assistant Examiner* — Jacqueline Brazin
(74) *Attorney, Agent, or Firm* — McDermott Will & Emery LLP

(57) ABSTRACT

A sensor device includes a flow path and a metal layer disposed in the flow path. The flow path is configured to allow a sample containing analytes to flow and to allow a carrier to be disposed therein. The carrier has acceptors that are fixed on a surface thereof and specifically bound with the analytes for producing aggregates. The flow path includes an aggregate trapping section at which the analytes locally concentrate to the section. This sensor device has high detection sensitivity with a simple structure.

29 Claims, 21 Drawing Sheets

(51) Int. Cl.
*G01N 21/03* (2006.01)
*G01N 21/05* (2006.01)
*G01N 21/77* (2006.01)
*G01N 21/552* (2014.01)
*B01L 3/00* (2006.01)

(52) U.S. Cl.
CPC ............ *G01N 21/05* (2013.01); *G01N 21/41* (2013.01); *G01N 21/553* (2013.01); *G01N 21/77* (2013.01); *B01L 2200/0668* (2013.01); *B01L 2300/069* (2013.01); *B01L 2400/043* (2013.01)

(58) Field of Classification Search
USPC ............................ 422/82.05, 82.08; 436/501
See application file for complete search history.

(56) References Cited

U.S. PATENT DOCUMENTS

| | | | |
|---|---|---|---|
| 6,696,022 B1 | 2/2004 | Chan et al. | |
| 6,859,570 B2* | 2/2005 | Walt et al. | ...................... 385/12 |
| 7,670,509 B2* | 3/2010 | Jin | ........................ B82Y 30/00 |
| | | | 252/500 |
| 2004/0096991 A1 | 5/2004 | Zhang | |
| 2004/0166025 A1* | 8/2004 | Chan | ....................... B01F 5/061 |
| | | | 422/400 |
| 2006/0154361 A1* | 7/2006 | Wikswo | ............ B01L 3/502746 |
| | | | 435/289.1 |
| 2007/0252982 A1* | 11/2007 | Wang et al. | ................... 356/301 |
| 2008/0218761 A1* | 9/2008 | Nishikawa et al. | .......... 356/445 |
| 2008/0223794 A1* | 9/2008 | Yamamichi | ........ B01J 20/28014 |
| | | | 210/767 |
| 2008/0260586 A1* | 10/2008 | Boamfa | ...................... 422/82.08 |
| 2010/0097611 A1* | 4/2010 | Song | .............................. 356/445 |
| 2010/0291711 A1* | 11/2010 | Atashbar | .............. G01N 27/127 |
| | | | 436/524 |
| 2011/0207238 A1* | 8/2011 | Horii | ................... B01L 3/50273 |
| | | | 436/518 |
| 2013/0010300 A1 | 1/2013 | Tamura et al. | |
| 2013/0029430 A1 | 1/2013 | Tamura et al. | |
| 2013/0040374 A1 | 2/2013 | Tachibana et al. | |

FOREIGN PATENT DOCUMENTS

| | | |
|---|---|---|
| TW | 224673 B | 12/2004 |
| WO | 2011/136344 A1 | 11/2011 |
| WO | 2011/142110 A1 | 11/2011 |
| WO | 2011/142118 A1 | 11/2011 |
| WO | WO 2011/142110 * | 11/2011 |

OTHER PUBLICATIONS

English Translation of Chinese Search Report dated Feb. 22, 2016 for the related Chinese Patent Application No. 201380012384.2.

* cited by examiner

SENSOR DEVICE

RELATED APPLICATIONS

This application is a national phase of International Application No. PCT/JP2013/000924, filed on Feb. 20, 2013, which in turn claims the benefit of Japanese Application No. 2012-047628, filed on Mar. 5, 2012, the disclosures of which Applications are incorporated by reference herein.

TECHNICAL FIELD

The present disclosure relates to a sensor device to be used for detecting, e.g. viruses.

BACKGROUND ART

FIG. 22 is a sectional view of sensor device 600 disclosed in Patent Literature 1 and to be used for detecting, e.g. viruses. Sensor device 600 includes prism 601, metal layer 602 disposed on a lower surface of prism 601 and having a flat surface, insulating layer 603 disposed on a lower surface of metal layer 602 and having a flat surface and a predetermined dielectric constant, and acceptor 604 fixed to a lower surface of insulating layer 603.

Surface plasmon wave (i.e. compression wave of electrons) exists at an interface between metal layer 602 and insulating layer 603. Light source 605 is disposed above prism 601 and supplies P-polarized incident light to prism 601 under a condition of total reflection. This incident light causes an evanescent wave on surfaces of metal layer 602 and insulating layer 603. The light totally reflected on metal layer 602 is received by detector 606 to detect an intensity of the light.

When a wave-number matching condition in which a wave number of the evanescent wave matches with a wave number of the surface plasmon wave is satisfied, the light energy supplied from light source 605 is used for exciting the surface plasmon wave, so that the intensity of the reflected light decreases. The wave-number matching condition depends on an incident angle of the light supplied from light source 605. Therefore, while the incident angle is changed, an intensity of reflected light is detected with detector 606. The intensity of the reflected light decreases at a certain incident angle.

A resonant angle at which the intensity of the reflected light takes a minimum value depends on the dielectric constant of insulating layer 603. When a specific bound substance is formed on the lower surface of insulating layer 603, the dielectric constant of layer 603 changes, and the resonant angle changes accordingly. This specific bound substance is produced by acceptor 604 and an analyte (i.e. a target to be measured in a sample) that are specifically bound together. By monitoring the change of the resonant angle, a binding strength of the specific bound substance or a speed of the binding can be detected.

CITATION LIST

Patent Literature

Patent Literature 1: Japanese Patent Laid-Open Publication No. 2005-181296

SUMMARY

A sensor device includes a flow path and a metal layer disposed in the flow path. The flow path is configured to allow a sample containing an analyte to flow therein and allow a carrier to be disposed therein. The carrier is configured to have acceptors fixed onto surfaces so that the acceptors are specifically bound with the analyte to produce an aggregate. The flow path includes an aggregate trapping section to allow the analytes to locally concentrate thereto. The sensor device has a high detection sensitivity with a simple structure.

DETAIL DESCRIPTION OF PREFERRED EMBODIMENTS

Exemplary Embodiment 1

Figure 1A:
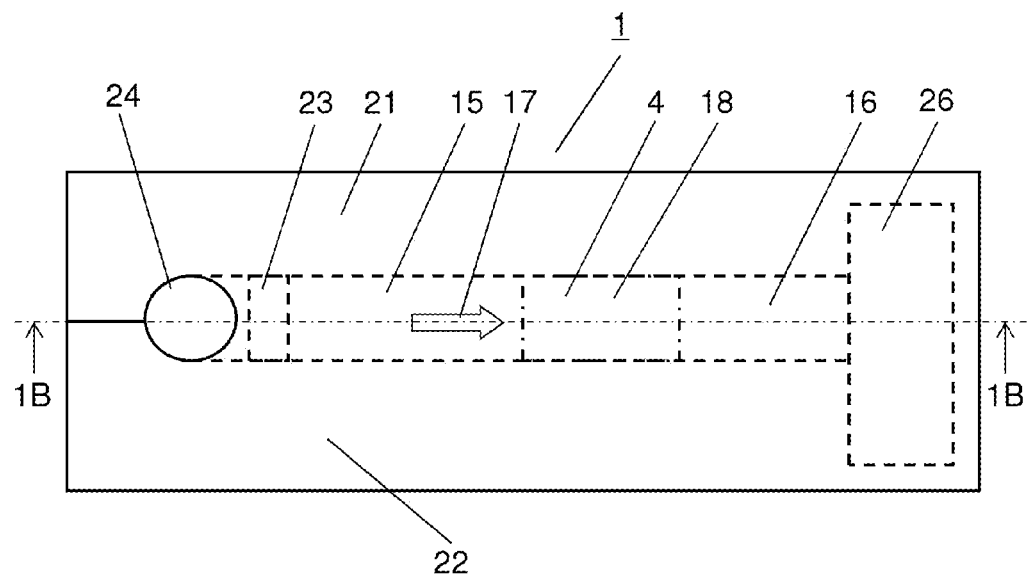
FIG. 1A is a top view of a sensor device in accordance with Exemplary Embodiment 1 of the present disclosure.
Figure 1B:
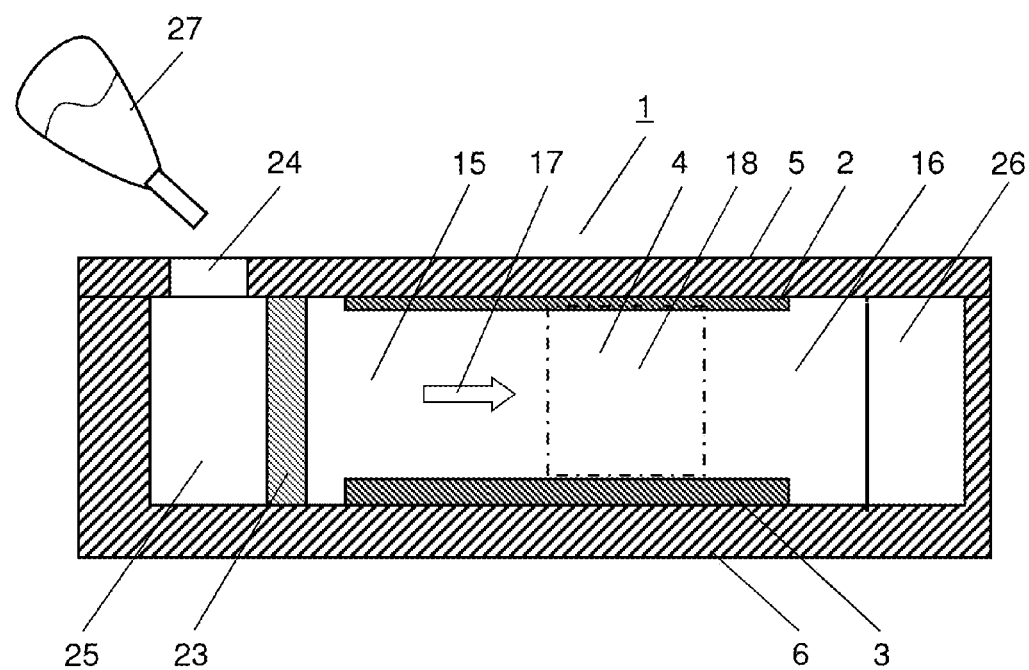
FIG. 1B is a sectional view of the sensor device at line 1B-1B shown in FIG. 1A.

FIG. 1A is a top view of sensor device 1 in accordance with Exemplary Embodiment 1 of the present disclosure. FIG. 1B is a sectional view of sensor device 1 at line 1B-1B shown in FIG. 1A. Sensor device 1 is a metal insulator metal (MIM) type device.

Sensor device 1 includes inlet 24 configured to have a sample injected therein, reservoir 25 temporarily reserving the injected sample, flow path 4 allowing the injected sample to flow therein, reservoir 26 retaining the sample having undergone an examination and flown through flow path 4, and metal layers 2 and 3 disposed on at least a part of flow path 4. A user injects the sample to be examined with pipette 27 through inlet 24 into reservoir 25. Flow path 24 includes holder 5 disposed at an upper section of sensor device 1 for holding metal layer 2, holder 6 disposed at a lower section of sensor device 1 for holding metal layer 3, side wall 21, and side wall 22. Flow path 4 includes specific region 18 sandwiched by metal layers 2 and 3, input region 15 disposed before specific region 18, and discharge region 16 disposed after specific region 18. The sample reserved in reservoir 25 is input due to a capillary phenomenon into input region 15 of flow path 4. The sample then flows in flow path 4 in a direction of arrow 17, and flows through region 18, then is discharged from discharge region 16, and is finally retained in reservoir 26. An analyte contained in the sample is trapped in region 18 of flow path 4 before being detected. Region 18 functions as an aggregate trapping section strapping an aggregate of the analyte.

Figure 2A:
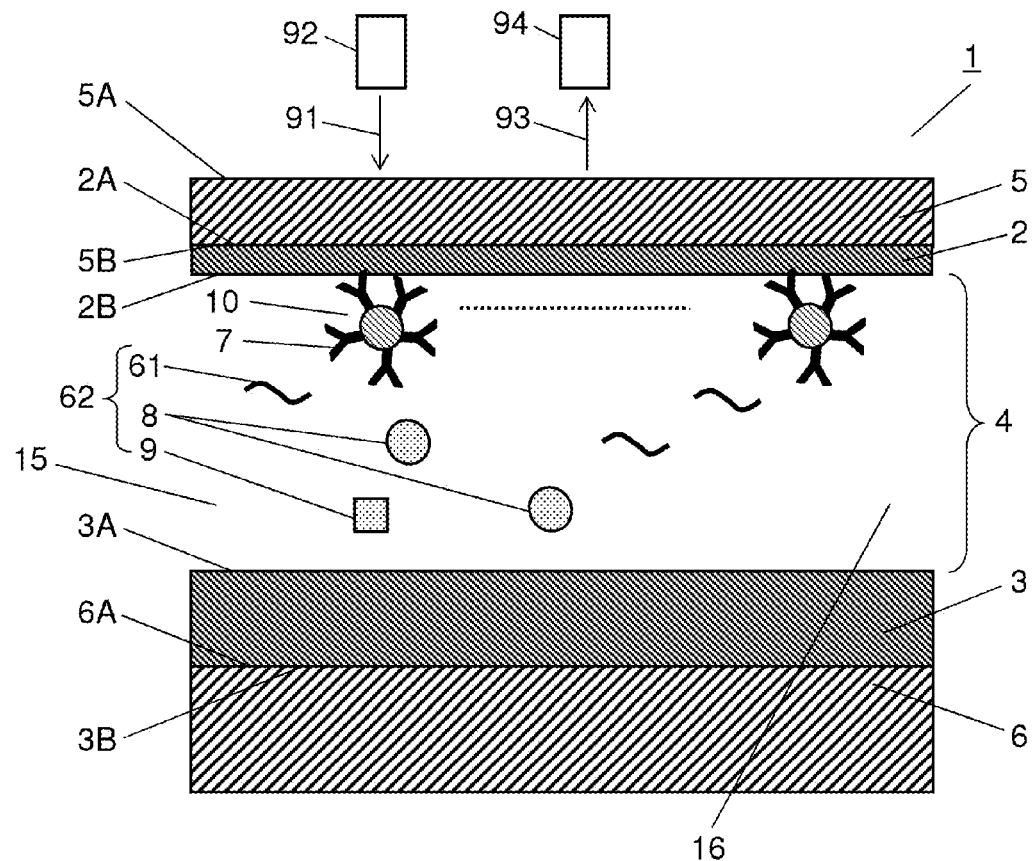
FIG. 2A is a side sectional view of a sensor device in accordance with Embodiment 1.
Figure 2B:
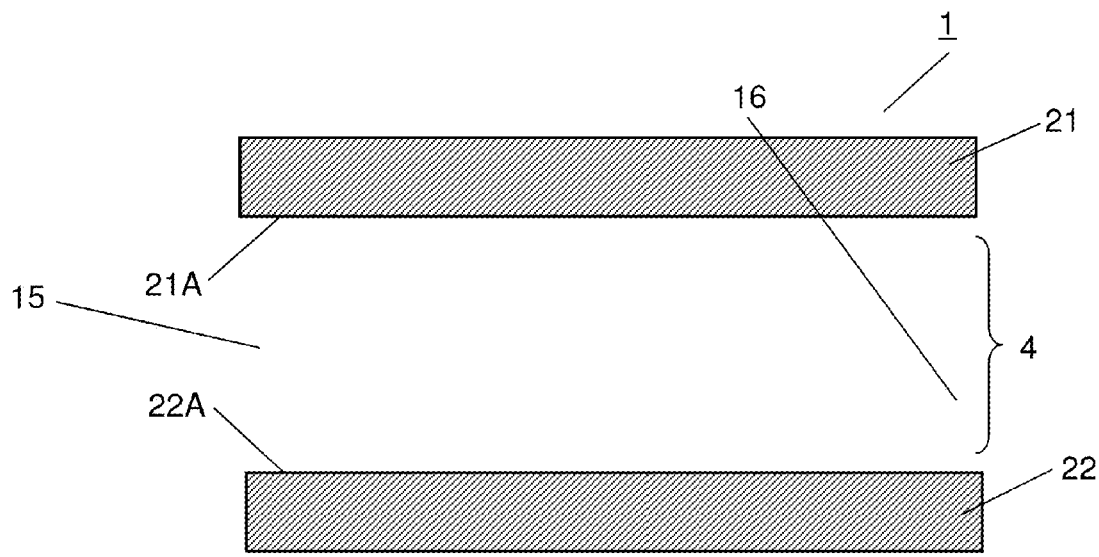
FIG. 2B is a top sectional view of the sensor device shown in FIG. 2A.

An operation of sensor device 1 will be described below. A region of flow path 4 sandwiched between metal layers 2 and 3 constitutes a detector. FIGS. 2A and 2B are a side sectional view and a top sectional view of an essential portion of sensor device 1. As shown in FIG. 2A, metal layer 3 faces metal layer 2 across flow path 4 and is disposed under metal layer 2. Metal layers 2 and 3 are made of metal, such as gold or silver. As shown in FIG. 2B, side wall 21 faces side wall 22 across flow path 4. Lower surface 2B of metal layer 2 constitutes an upper surface of flow path 4, and upper surface 3A of metal layer 3 constitutes a lower surface of flow path 4. Side surface 21A of side wall 21 constitute a first side surface of flow path 4, and side surface 22A of side wall 22 constitutes a second side surface of flow path 4. Flow path 4 is thus constituted by these four surfaces. Carriers 10 are fixed physically by weak force, such as van der Waals force, and adheres onto at least one of lower surface 2B of metal layer 2 and upper surface 3A of metal layer 3. Carrier 10 includes acceptors 7 which are fixed onto surfaces of a substance made of metal or resin and which are specifically bound with analyte 8.

The substance made of metal or resin preferably has a size not larger than 10% of a wavelength of an incident electromagnetic wave supplied from above the sensor device 1. The size of the substance refers to, e.g. the diameter of the substance. The wavelength refers to a wavelength that takes into account an influence of refraction index in flow path 4. The size of the substance made of metal or resin exceeding 1/10 of the wavelength of the supplied electromagnetic wave increases an effect of Mie Scattering while the size is not larger than 1/10 of the wavelength increases an effect of Rayleigh Scattering. However, the scattering intensity of Rayleigh Scattering is so small because it is proportional to minus sixth-power of a radius of the substance, so that the scattering affects almost nothing. The size not greater than 1/10 of the wavelength thus can improve the sensitivity of sensor device 1. Greater influence produced by the scattering will cause light to lose straightness, so that the light cannot be correctly observed. When visible light having a wavelength of ranging from 500 to 600 nm to be used for observation among others is used as the electromagnetic wave to be supplied from over the sensor device 1, the size of the substance made of metal or resin is preferably not greater than 50 to 60 nm.

When sensor device 1 is in operation, sample 62 is supplied into flow path 4 through input region 15 to fill flow path 4, and then sample 62 is discharged from discharge region 16. Sample 62 in flow path 4 is thus actually sandwiched between metal layers 2 and 3. Sample 62 contains analyte 8, non-specific specimen 9, and medium 61. Medium 61 is a fluid, such as liquid or gel, and carries analyte 8 and non-specific specimen 9.

Metal layer 2 has a thickness not larger than 100 nm, so that it cannot maintain its shape by itself. Upper surface 2A of metal layer 2 is fixed to lower surface 5B of holder 5 for maintaining its shape. Metal layer 3 is fixed to upper surface 6A of holder 6 to maintain its shape.

Electromagnetic wave 91 enters from upper surface 2A of metal layer 2. In the case that electromagnetic wave 91 is visible light and metal layer 2 is made of gold, metal layer 2 preferably has a thickness ranging from 10 nm to 45 nm.

In the case that metal layer 3 is made of gold, metal layer 3 preferably has a thickness not smaller than 100 nm. If the thickness is smaller than 100 nm, incident electromagnetic wave 91 of visible light passing through metal layer 3, and decreases an amount of electromagnetic wave 91 reflected in flow path 4.

Electromagnetic wave source 92 is disposed above upper surface 2A of metal layer 2, namely, it is opposite to metal layer 3 with respect to metal layer 2. Electromagnetic wave source 92 supplies electromagnetic wave 91 from above upper surface 2A to metal layer 2.

Acceptor 7 refers to a trapper that is specifically bound with a designated analyte, and is, for example, antibody, receptor protein, aptamer, porphyrin, and polymer produced by molecular imprint technique.

As shown in FIG. 1B, filter 23 is preferably disposed between reservoir 25 and flow path 4 for removing unnecessary substance, such as dust, mixed in the sample.

An operation of sensor device 1 will be described below. According to Embodiment 1, electromagnetic wave 91 is light, and electromagnetic wave source 92 is a light source.

The electromagnetic wave enters from above metal layer 2 to upper surface 2A at incident angle θ. A part of the wave reflects on upper surface 2A and lower surface 2B and propagates upward from metal layer 2 in a direction of reflection angle −θ. Incident angle θ is an angle between a normal line of the upper surface of metal layer 2 and an incident direction of the electromagnetic wave. The electromagnetic wave reflected on metal layer 2 and propagating upward from metal layer 2 at angle −θ is referred to as a first electromagnetic wave. Most of the electromagnetic wave not reflected on upper surface 2A or lower surface 2B of metal layer 2 passing through metal layer 2 propagates in flow path 4 and reaches upper surface 3A of metal layer 3. In the case that metal layer 3 has a thickness not smaller than 200 nm, the electromagnetic wave propagating from above metal layer 3 is entirely reflected on metal layer 3, and propagates in flow path 4 again toward lower surface 2B of metal layer 2. Parts of the electromagnetic wave reaching lower surface 2B of metal layer 2 passes through metal layer 2 and propagates upward from metal layer 2 at angle −θ. The electromagnetic wave passing through metal layer 2 from flow path 4 and propagating upward from metal layer 2 at angle −θ is referred to as a second electromagnetic wave. Most of the electromagnetic wave propagating from lower surface 2B of metal layer 2 but not passing through metal layer 2 is reflected on lower surface 2B and upper surface 2A of metal layer 2, and then propagates in flow path 4 downward. The first electromagnetic wave and the second electro-magnetic wave above metal layer 2 interfere with each other. The interference condition satisfies formula (1) or (2) with an integer m, the wavelength λ of the electromagnetic wave in vacuum, a thickness d of flow path 4 (i.e. a space d between the lower surface of metal layer 2 and the upper surface of metal layer 3), a refraction index n within a hollow region, and the incident angle θ.

$$(m+\tfrac{1}{2}) \times \lambda = 2 \times n \times d \times \cos\theta \quad \text{(Formula 1)}$$

$$m \times \lambda = 2 \times n \times d \times \cos\theta \quad \text{(Formula 2)}$$

When space d satisfies formula (1), the first and second electromagnetic waves weaken each other. When space d satisfies formula (2), the first and second electromagnetic waves strengthen each other.

The interference condition can be controlled with the shapes (depending mainly on the thickness) of metal layers 2 and 3, the space between metal layer 2 and metal layer 3, dielectric constant (refraction index) of metal layer 2, dielectric constant (refraction index) of metal layer 3, and the refraction index in flow path 4.

Detector 94 is disposed above upper surface 2A of metal layer 2 and is configured to detect electromagnetic wave 93, such as light. When sensor device 1 receives electromagnetic wave 91 supplied from electro-magnetic wave source 92, detector 94 receives electromagnetic wave 93, such as light, reflected or radiated from sensor device 1. Detector 94 is may not necessary. In the case that electromagnetic wave 91 is visible light, the user can visibly sense a change in color or an intensity of electromagnetic wave 91, hence providing simple and inexpensive sensor device 1.

Holder 5 is made of material preventing electromagnetic wave 91 from attenuating so as to efficiently supply electromagnetic wave 91 to metal layer 2. According to Embodiment 1, since electromagnetic wave 91 is light, holder 5 is made of transparent material, such as glass or transparent plastic, so as to allow the light to pass through holder 5 efficiently. Holder 5 preferably has a thickness as small as possible, and has a predetermined mechanical strength.

The supplied electromagnetic wave 91, such as light, does not preferably pass through metal layer 3 so as to increase the sensitivity of sensor device 1, so that holder 6 may be preferably made of material that cuts off electromagnetic wave 91, such as light. For instance, holder 6 may be made of metal or semiconductor having a thickness not smaller than 100 nm.

In sensor device 1, plural carriers 10 are disposed on lower surface 2B of metal layer 2 facing flow path 4. Each of carriers 10 includes plural acceptors 7 fixed onto a surface of a substance made of metal or resin.

Figure 3:
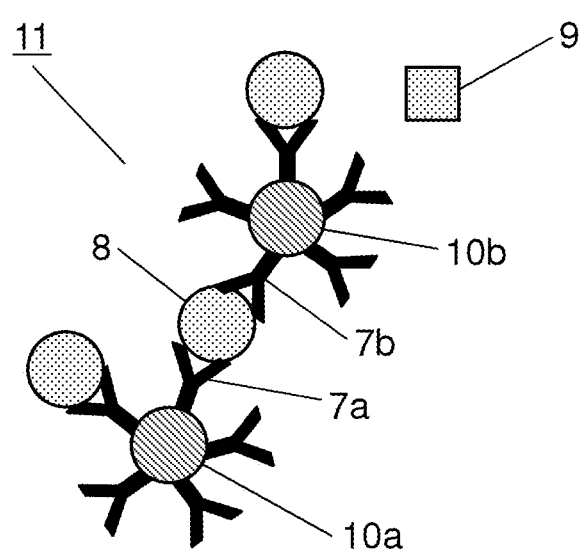
FIG. 3 is a schematic view of the sensor device in accordance with Embodiment 1 for illustrating a specific binding between an acceptor and an analyte.

When analyte 8 in sample 62 contacts one of acceptors 7 attached to carrier 10, acceptor 7 is specifically bound with analyte 8. FIG. 3 is a schematic view of sensor device 1 according to Embodiment 1 for illustrating the specific binding of acceptor 7 and analyte 8 of carrier 10. As shown in FIG. 3, sample 62 contains analyte 8 to be detected and non-specific specimen 9. Acceptor 7 attached to carrier 10 is not specifically bound with non-specific specimen 9, but is specifically bound only with analyte 8, and then plural carriers 10 couple with each other via analyte 8, thereby forming aggregate 11. For instance, carrier 10a has plural acceptors fixed on a surface thereof, and one acceptor 7a out of the plural acceptors is specifically bound with analyte 8. Carrier 10b includes plural acceptors fixed on a surface thereof, and one acceptor 7b out of the plural acceptors is specifically bound with analyte 8. Two carriers 10a and 10b form one aggregate 11 with analyte 8 between carriers 10a and 10b. Each of carriers 10a and 10b includes plural acceptors, so that these acceptors are specifically bound with other analytes for coupling a large number of carriers together, thereby providing a large size of aggregate. In FIGS. 2A and 2B, sensor device 1 has carriers 10 placed only on lower surface 2B of metal layer 2; however, carriers 10 may be placed on upper surface 3A of metal layer 3 in addition to lower surface 2B, or carriers 10 can be placed only on upper surface 3, not on lower surface 2B.

Figure 4A:
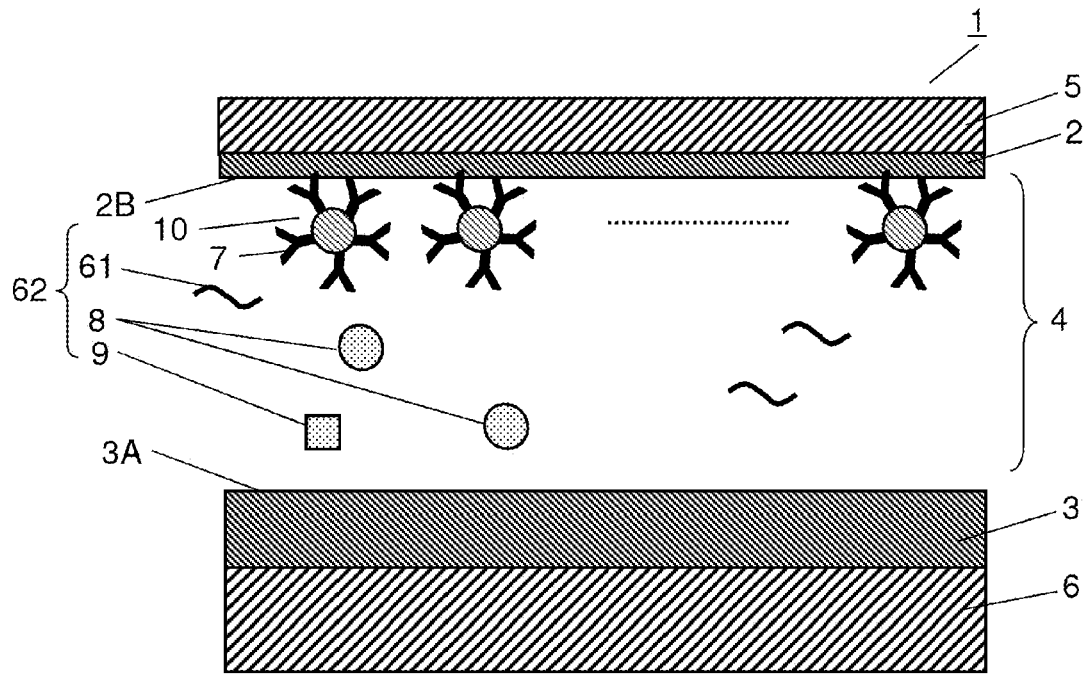
FIG. 4A is a side sectional view of the sensor device in accordance with Embodiment 1.
Figure 4B:
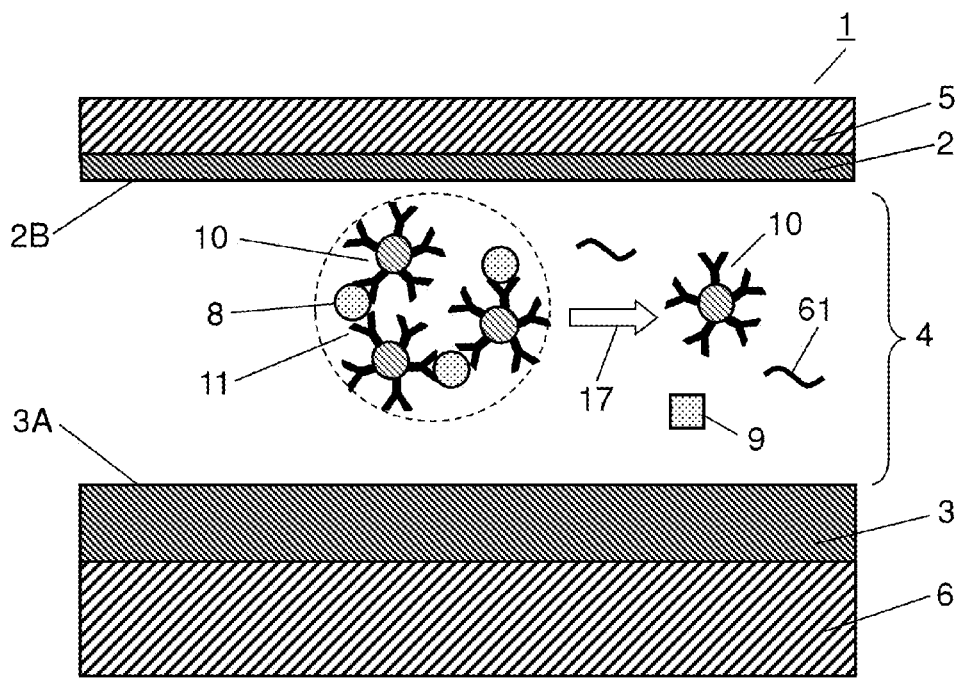
FIG. 4B is a side sectional view of the sensor device in accordance with Embodiment 1.

FIGS. 4A and 4B are side sectional views of sensor device 1 in accordance with Embodiment 1 for illustrating the operation. As shown in FIG. 4A, carriers 10 are physically adsorbed and fixed onto lower surface 2B of metal layer 2 in advance in flow path 4 that is vacuumed or filled with air. Sample 62 of liquid containing non-specific specimen 9 and analyte 8 input into flow path 4 changes a status in flow path 4, particularly the dielectric constant (refraction index) in flow path 4. This allows the electromagnetic waves interfere with each other and strengthen or weaken each other above metal layer 2 according to formulae (1) and (2). The wavelengths λ of the electromagnetic waves interfering with each other changes, so that a frequency distribution of the electromagnetic wave detected by detector 94 changes. As discussed above, the detection of changes in the electromagnetic wave that propagates upward from metal layer 2 allows the user to realize the presence of the specific binding in flow path 4.

As shown in FIG. 4B, sample 62 input in flow path 4 is forced by external force to flow along arrow 17. Carriers 10 disposed on lower surface 2B of metal layer 2 is physically fixed onto lower surface 2B by weak force (e.g. van der Waals force), so that the flow can remove carriers 10 from lower surface 2B. Carriers 10 are then suspended in flow path 4 and flow along arrow 17. While carriers 10 flow in flow path 4, acceptors 7 and analytes 8 of carriers 10 are specifically bound together, and other carriers 10 are also specifically bound with these analytes 8. This process is repetitively performed, thereby forming aggregate 11 which is heavier than carrier 10, non-specific specimen 9, and medium 61, so that aggregate 11 flows rather slowly. When aggregate 11 is trapped at specific region 18 (aggregate trapping section) in flow path 4, a dielectric constant of region 18 changes, so that a dielectric constant (refraction index) of medium 61 disposed between metal layers 2 and 3 may change, thus changing a distribution of the dielectric constants. These changes the state of the electromagnetic wave propagating upward from metal layer 2 as derived from formulae (1) and (2). The detection of the changes in the electromagnetic wave propagating upward from metal layer 2 allows the user to realize the status of the specific binding between acceptors 7 and analytes 8, to be more specific, the user will know strength of the specific binding and a speed of the binding.

Figure 5:
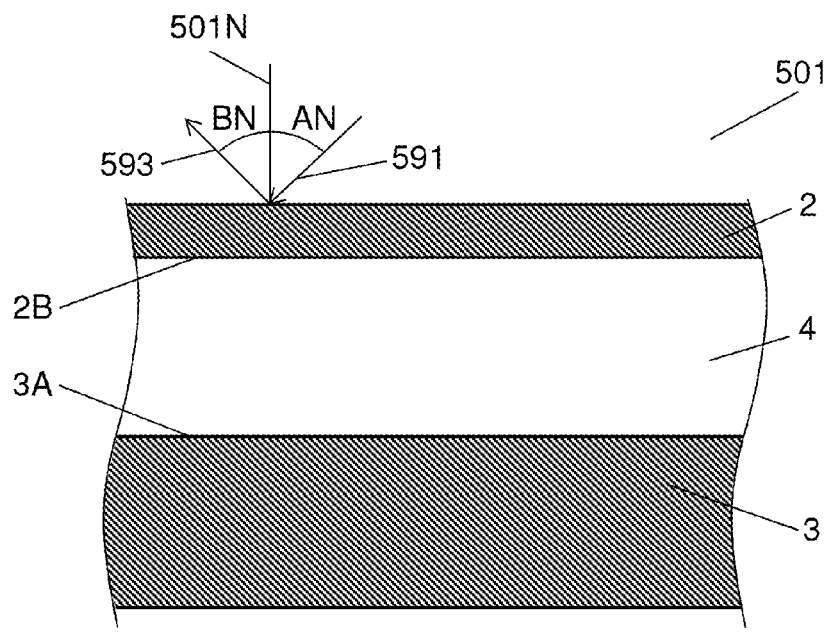
FIG. 5 is a schematic view of an analysis model of electromagnetic field simulation of the sensor device in accordance with Embodiment 1.

The specific binding between acceptor 7 and analyte 8 changes the state of the electromagnetic wave propagating upward from metal layer 2. This change will be described with a result of electromagnetic field simulation. FIG. 5 is a schematic view of an analysis model of the electromagnetic field simulation of sensor device 1 according to Embodiment 1.

In analysis model 501 shown in FIG. 5, metal layer 2 is made of silver and has a thickness of 30 nm. Metal layer 3 is made of silver and has a thickness of 130 nm. Metal layer 2 is spaced away from metal layer 3 by 160 nm. Flow path 4 is filled with air having a relative dielectric constant of 1. A portion above upper surface 2A of metal layer and a portion below lower surface 3B of metal layer 3 are filled with air. In analysis model 501, electromagnetic wave 591 enters into metal layer 2 at incident angle AN, and electromagnetic wave 593 propagates upward from metal layer 2 at angle BN (=−AN). These electromagnetic waves are analyzed by the simulation. In analysis model 501, metal layers 2 and 3 and flow path 4 extend infinitely in horizontal directions.

Figure 6:
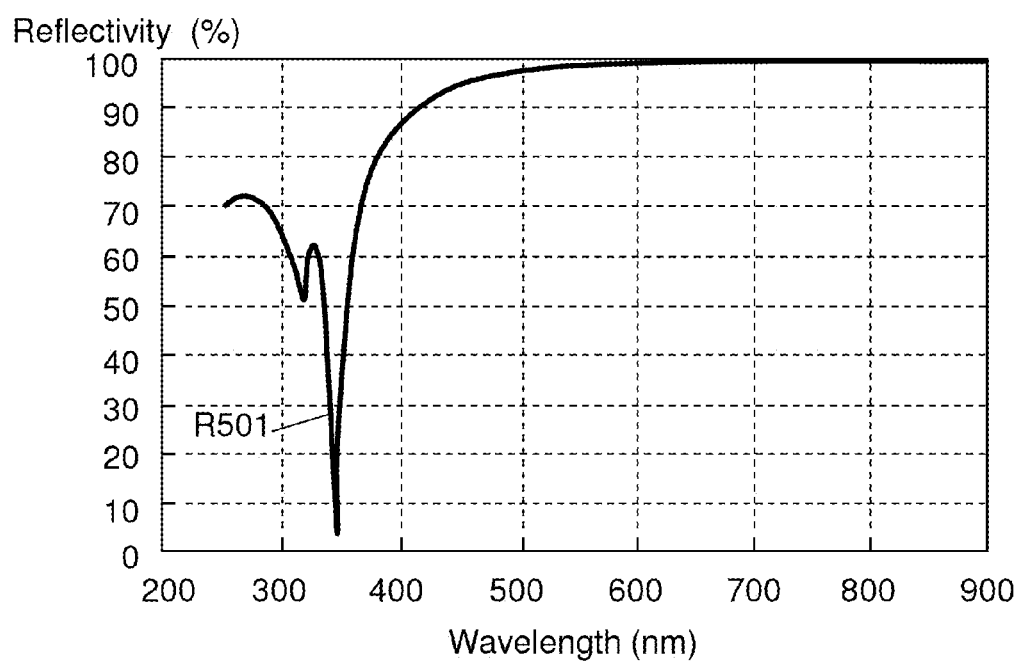
FIG. 6 shows an analysis result of the electromagnetic field simulation of the sensor device in accordance with Embodiment 1.

Sensor device 1 detects not only a change in frequency or wavelength at which the first and second electromagnetic waves weaken each other, but also a change in reflectivity R501 that is a ratio of the energy of the incident electromagnetic wave entering into metal layer 2 to the energy of the electromagnetic wave propagating upward from metal layer 2. Use of two indexes (i.e. frequency or wavelength, and wavelength) simultaneously allows detecting a change in the state of the medium of flow path 4, so that sensor device 1 can obtain high detective capability. The status of the medium refers to a status of the substance filling partially or entirely flow path 4, for instance, a composition of the substance itself or a distribution of the substance in flow path 4. FIG. 6 shows a result of the analysis model shown in FIG. 5. In FIG. 6, the horizontal axis represents wavelength, and the vertical axis represents reflectivity R501. As shown in FIG. 6, an electromagnetic wave having a wavelength of about 340 nm satisfies formula (1) that allows canceling out two electromagnetic waves, so that a reflectivity decreases remarkably at the wavelength of about 340 nm.

Sensor device 1 can be used as a simple and home-use influenza-virus sensor. In this case, a sample containing human saliva is injected into flow path 4. A home-use sensor device needs to have higher detection sensitivity and better usability than a professional-use sensor device. To achieve this need, analytes 8 concentrate locally to specific region 18 of flow path 4, thereby increasing a density of analyte 8 in region 18. Electromagnetic wave source 92 preferably employs a visible light source so that users can sense a change in wavelength easily without using a special detector expressly.

Figure 7A:
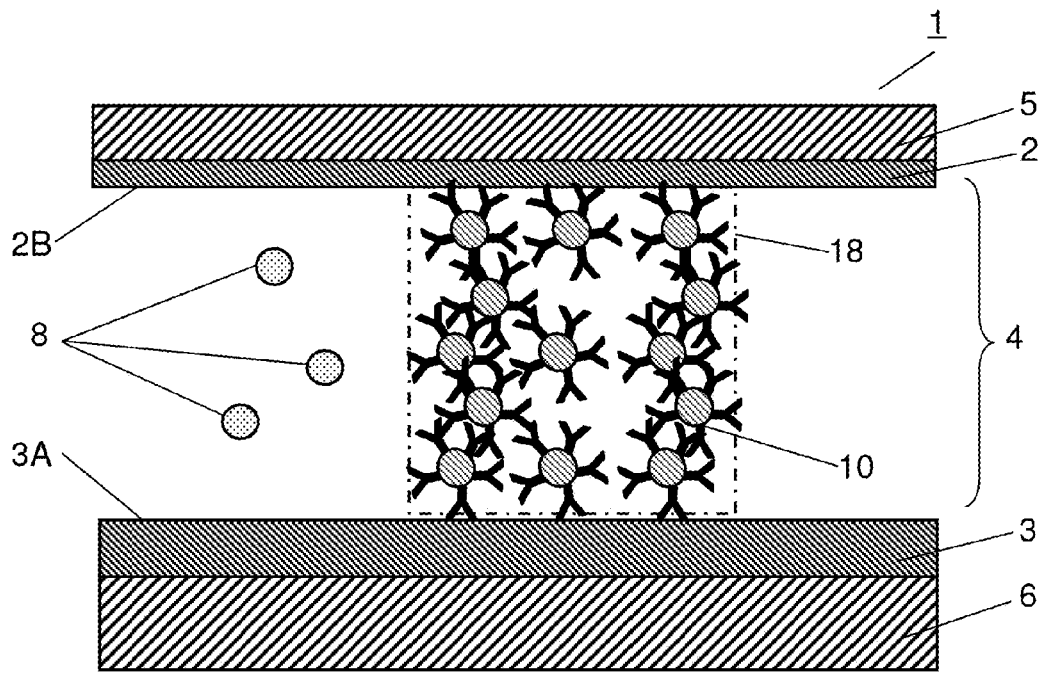
FIG. 7A is a side sectional view of the sensor device in accordance with Embodiment 1.
Figure 7B:
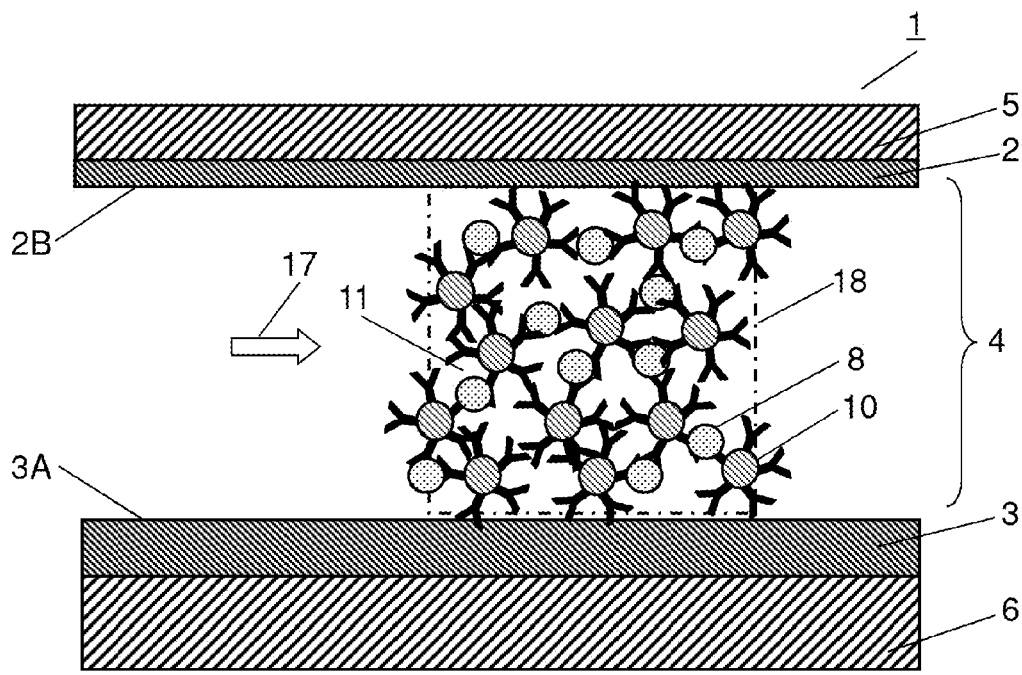
FIG. 7B is a side sectional view of the sensor device in accordance with Embodiment. 1

A structure of sensor device 1 according to Embodiment 1 for allowing analytes 8 to concentrate locally to the specific region in flow path 4 will be described below. FIGS. 7A and 7B are side sectional views of the sensor device in accordance with Embodiment 1. In this sensor device, analytes concentrate locally. FIG. 7A shows a status in flow path 4 just before a sample has been input. FIG. 7B shows a status in flow path 4 after the sample is input and then a predetermined time has passed. Hereinafter, only analyte 8 is shown as sample 62, and both of medium and specimen are not shown in FIGS. 7A and 7B, and figures thereafter.

As shown in FIG. 7A, plural carriers 10 concentrate locally at specific region 18 (aggregate trapping section) between lower surface 2B of metal layer 2 and upper surface 3A of metal layer 3, and are fixed by physical adsorption. To be more specific, a density of carriers 10 physically adsorbed at region 18 is higher than other carriers 10 at further regions in flow path 4. The physical adsorption is caused by van der Waals force acting on the interface between carriers 10 and each of metal layers 2 and 3, and acting on the interface between carriers 10. After sample 62 is input as shown in FIG. 7A, and the predetermined time lapses, then aggregate 11 including analytes 8 is formed. Specific region 18 is filled with aggregates 11 as shown in FIG. 7B. In other words, specific region 18 functions as an aggregate trapping section for trapping the aggregates. In this case, a large number of carriers 10 have been fixed at region 18 from the beginning, so that the dielectric constant at region 18 is not so much changed. The interference condition between the electromagnetic waves propagating upward from metal layer 2 does not change from before the aggregation to after the aggregation. As a result, no change is found in color of the reflection light between before and after the sample input. On the other hand, when sample 62 has no analytes, aggregate 11 cannot be formed, so that carriers 10 flow together with sample 62 in flow path 4 and are discharged from region 18. The dielectric constant at region 18 changes more significantly than the case where analytes 8 form aggregates 11, and the status of the interference between the electromagnetic waves propagating upward from metal layer 2 changes. As a result, the incident light including a visible-light band entering into sensor device 1 changes in color of the light propagating upward from metal layer 2 comparing with the color before inputting the sample. This color change can be sensed by human eyes, thereby recognizing the presence of analytes 8 in sample 62. Thus, sensor device 1 allowing a user to realize easily at home whether or not analytes (e.g. virus) exist is provided. A structure for preventing aggregates 11 from flowing out easily from region 18 due to the flow of sample 62 along arrow 17 may be formed at region 18. This structure retains the aggregates within region 18, and is formed by, for instance, roughening at least one surface of metal layers 2 and 3 facing region 18, thereby increasing a friction coefficient thereof.

Figure 8A:
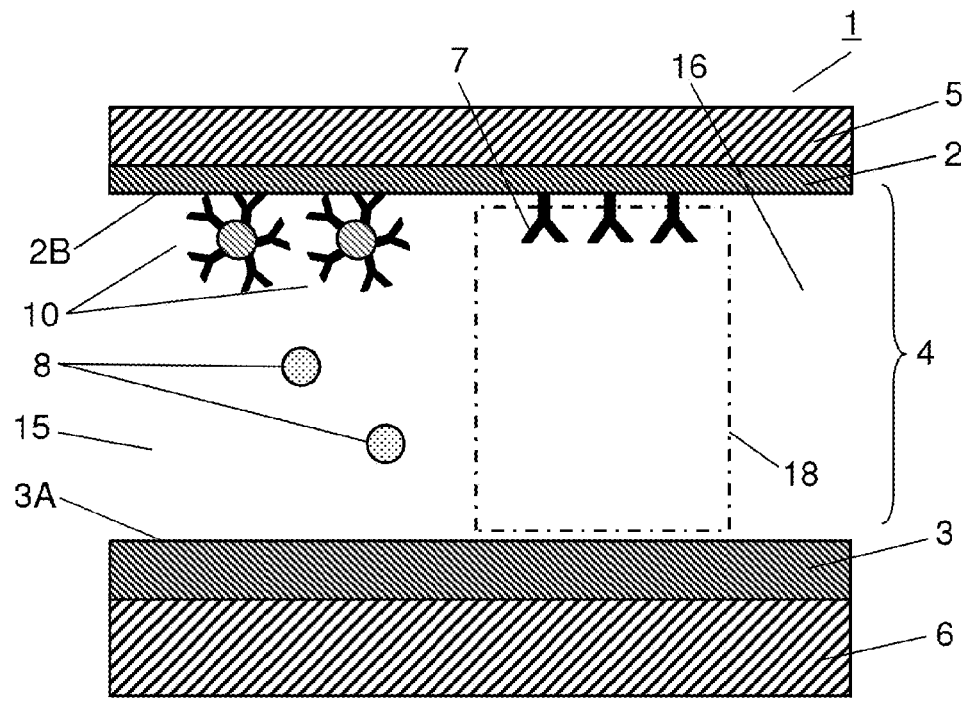
FIG. 8A is a side sectional view of the sensor device in accordance with Embodiment 1.
Figure 8B:
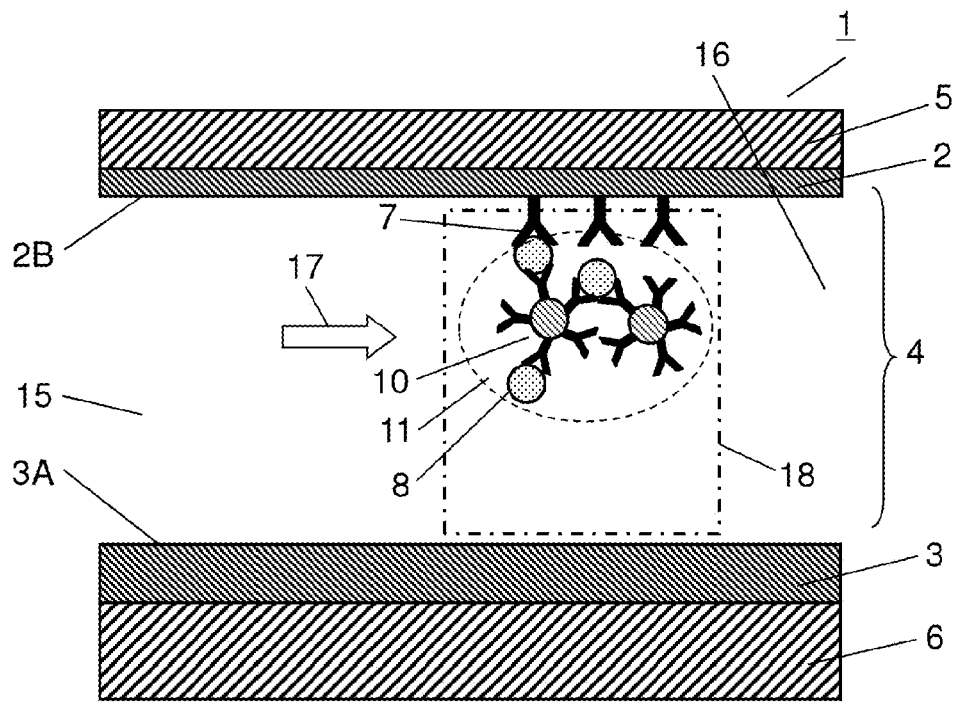
FIG. 8B is a side sectional view of the sensor device in accordance with Embodiment 1.

FIGS. 8A and 8B are side sectional views of sensor device 1 in which analytes 8 concentrate locally. FIG. 8A shows a status in flow path 4 just before the sample is input to flow path 4. FIG. 8B shows a status in flow path 4 after the sample is input and then a predetermined time lapses. As shown in FIG. 8A, plural acceptors 7 concentrate locally and are fixed to specific region 18 on lower surface 2B of metal layer 2 by chemical adsorption. Acceptors 7 do not exist at the other regions in flow path 4. Plural carriers 10 are fixed onto lower surface 2B by physical adsorption at a position from region 18 toward input region 15. In the status shown in FIG. 8A, a sample containing analytes 8 is input into flow path 4, and a predetermined time lapses. Then, as shown in FIG. 8B, the flow of sample removes carriers 10 from lower surface 2B of metal layer 2, and carriers 10 are suspended in flow path 4 to be specifically bound with analytes 8, thereby forming aggregates 11. Aggregates 11 follow the flow of the sample along arrow 17, and are specifically bound with plural acceptors 7 disposed on lower surface 2B via analytes 8 at region 18 (aggregate trapping section).

As a result, aggregates 11 containing analytes 8 are trapped at region 18, thereby causing analytes 8 in the sample to concentrate locally at region 18. In this case, since aggregates 11 containing analytes 8 are trapped at region 18, the dielectric constant at region 18 is drastically different from dielectric constants of the other regions, so that sensitivity to the analytes increases. In other words, a status of the electromagnetic wave (e.g. a color of the visible light) propagating upward form metal layer 2 contacting region 18 of flow path 4 is different from that of the electromagnetic wave propagating upward from metal layer 2 contacting the regions other than region 18. This phenomenon allows a user to visibly recognize easily at home whether the analytes exist or not. In the case of chemical adsorption, since acceptors 7 are adsorbed and fixed by covalent binding onto lower surface 2B of metal layer 2, acceptors 7 can be fixed to aggregates 11 more firmly than in the case of physical adsorption. Aggregates 11 can be thus fixed in more concentrated easily at region 18 where the analytes are expected to be detected, hence providing sensor device 1 with high sensitivity.

Figure 22:
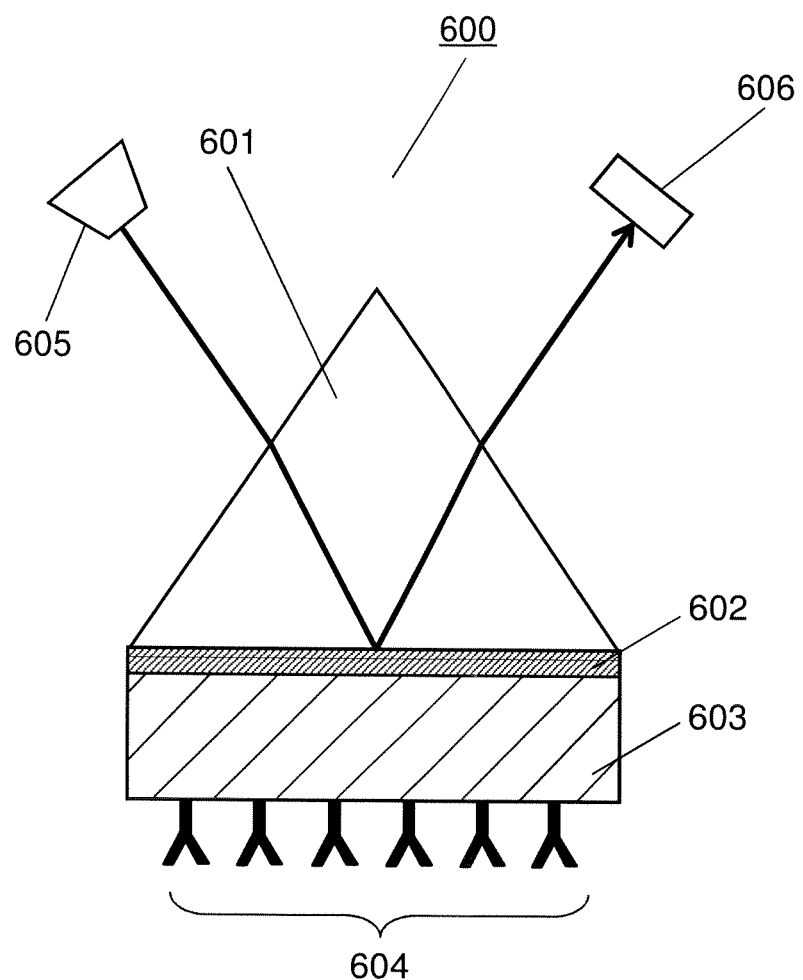
FIG. 22 is a sectional view of a conventional sensor device.

In conventional sensor device 600 shown in FIG. 22, analytes that are dispersed in a sample are specifically bound with acceptors fixed on a lower surface of insulating layer 603, so that the detection sensitivity is insufficient.

Figure 9:
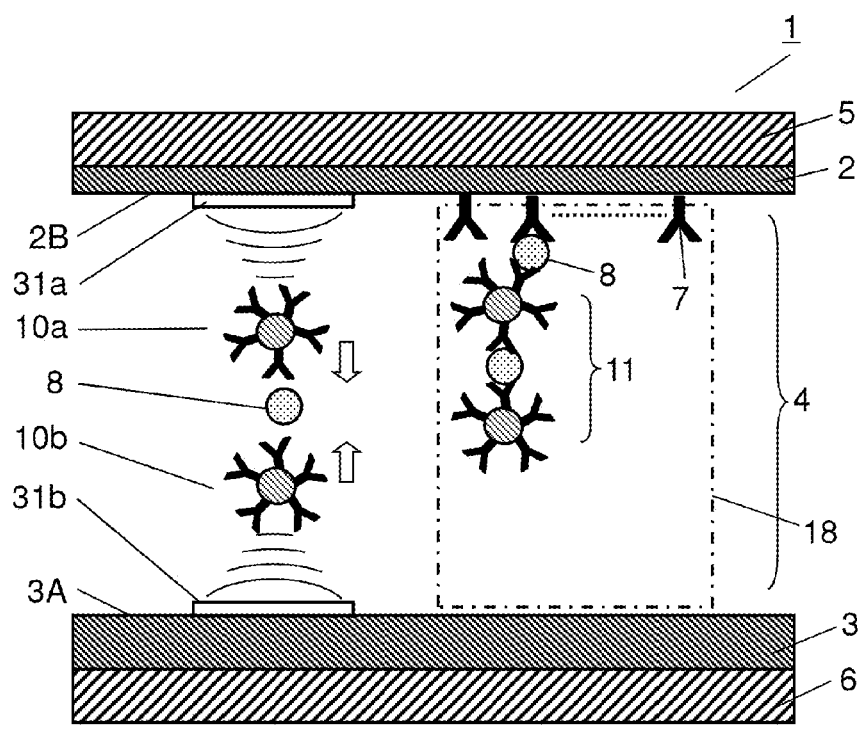
FIG. 9 is a side sectional view of the sensor device in accordance with Embodiment 1.

A structure for facilitating the aggregating speed to form aggregates 11 will be described below. FIG. 9 is a side sectional view of sensor device 1 shown in FIGS. 8A and 8B for illustrating the structure for facilitating the aggregation with ultrasonic wave. Sensor device 1 shown in FIG. 9 further includes ultrasonic wave generator 31a disposed on a portion of lower surface 2B of metal layer 2 and ultrasonic wave generator 31b disposed on a portion of upper surface 3A of metal layer 3. Carriers 10a and 10b above flow path 4 are moved by the ultrasonic waves generated by ultrasonic wave generators 31a and 31b to be easily bound with analytes 8. A standing wave of ultrasonic wave is generated between metal layers 2 and 3, so that carriers 10 and analytes 8 concentrate at a predetermined region between layers metal 2 and 3, accordingly increasing the possibility of binding carriers 10 with analytes 8. Carriers 10a and 10b are thus specifically bound with analytes 8 to form aggregates 11. Then, aggregates 11 then are trapped at region 18 via analytes 8 by acceptors 7 disposed on lower surface 2B of metal layer 2. The ultrasonic wave generated from an upper section and a lower section in flow path 4 facilitates the specific binding between carriers 10 and analytes 8, hence facilitating the aggregation of analytes 8. The ultrasonic wave generator may be disposed on only one of lower surface 2B and upper surface 3A. The ultrasonic wave generator may be disposed on side surface 21A of side wall 21 or side surface 22A of side wall 22. These walls constitute flow path 4. The ultrasonic wave generator can be disposed on a portion of lower surface 5B of holder 5 at which metal layer 2 is not formed or on a portion of upper surface 6A of holder 6 at which metal layer 3 is not formed.

Figure 10:
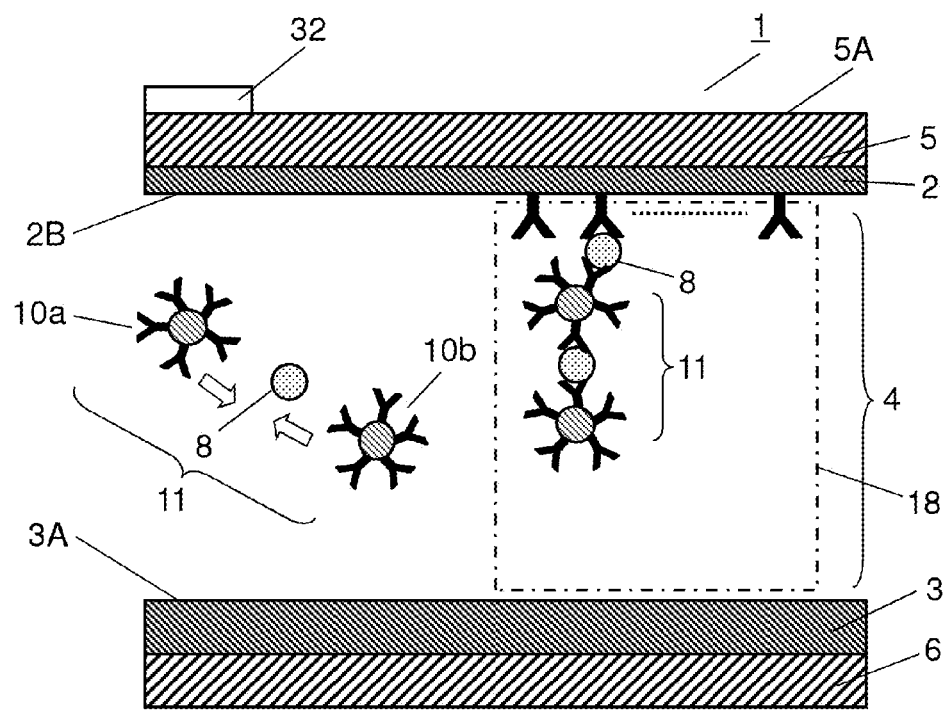
FIG. 10 is a side sectional view of the sensor device in accordance with Embodiment 1.

FIG. 10 is a side sectional view of sensor device 1 in which flow path 4 is heated to raise a temperature for facilitating the aggregation. Sensor device 1 shown in FIG. 10 further includes heater 32 as a heat source disposed on upper surface 5A of holder 5. Heater 32 heats a sample in flow path 4 to increase kinetic energies of carriers 10 and analytes 8, thereby facilitating the specific binding. For instance, facilitating of movements of carrier 10a, carrier 10b, and analyte 8 increases the possibility for them to contact each other, accordingly inviting them to be specifically bound with each other, and forming aggregates 11. Carriers 10a and 10b are thus specifically bound with analytes 8, and form aggregates 11. Aggregates 11 are then trapped at region 18 via analytes 8 by acceptors 7 disposed on lower surface 2B of metal layer 2. The heating of flow path 4 of sensor device 1 encourages the specific binding between carriers 10 and analytes 8, thereby facilitating the aggregation of analytes 8. The location of heater 32 is not limited to a certain place as far as it can heat the sample.

Figure 11:
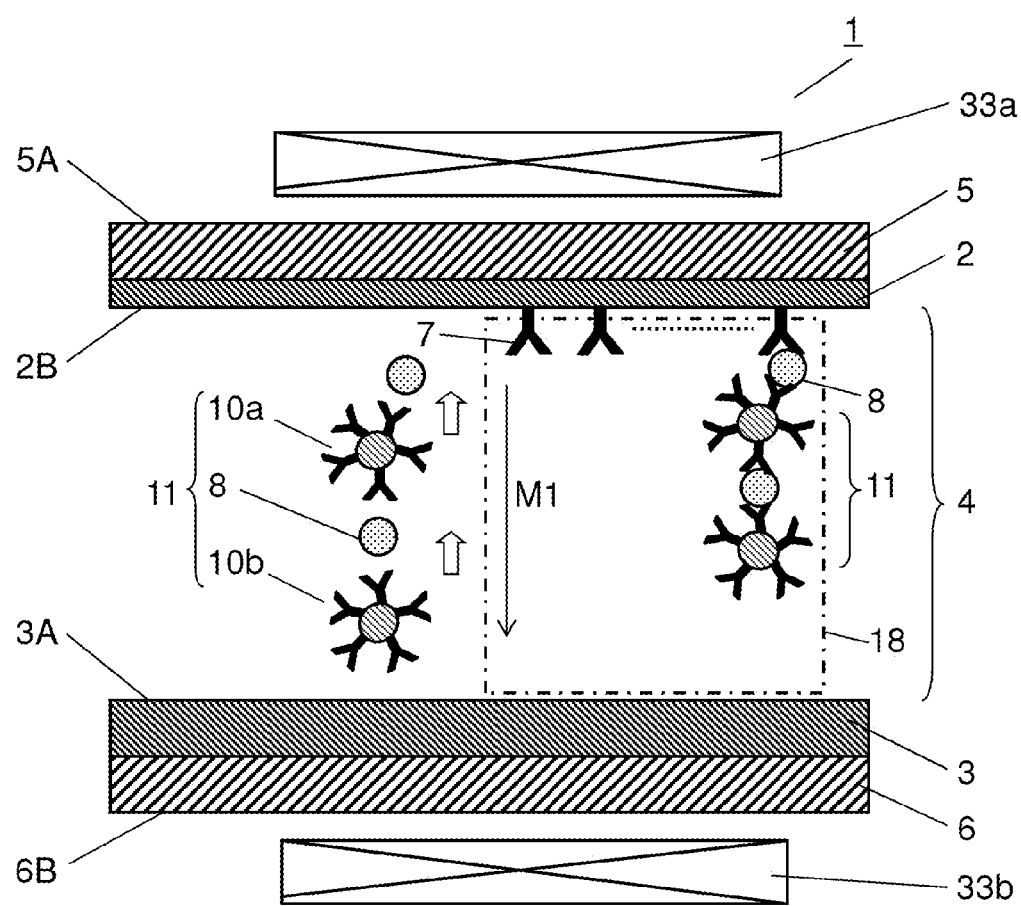
FIG. 11 is a side sectional view of the sensor device in accordance with Embodiment 1.

FIG. 11 is a side sectional view of sensor device 1 in which magnetic field is applied to flow path 4 for facilitating the aggregation. Sensor device 1 shown in FIG. 11 further includes magnetic field generators 33a and 33b which are disposed near upper surface 5A of holder 5 and lower surface 6B of holder 6, respectively. Magnetic field generators 33a and 33b generate magnetic field M1 directing from an upper section of flow path 4 toward a lower section of flow path 4. Carriers 10 are preferably made of magnetic material such that carriers 10 can be attracted along the direction of magnetic field M1. Carriers 10a and 10b made of magnetic material move upward by magnetic field M1, and tend to be bound with analytes 8. Carriers 10a and 10b are thus specifically bound with analytes 8 and form aggregates 11. Aggregates 11 are then trapped at region 18 by acceptors 7 via analytes 8. Magnetic field M1 generated along the vertical direction of flow path 4 promotes the specific binding between carriers 10 and analytes 8, thereby facilitating the aggregation of analytes 8. Instead of providing sensor device 1 with magnetic field generators 33a and 33b, a user can hold a magnetic field generator with a hand and apply magnetic field M1 to the flow path.

Figure 12:
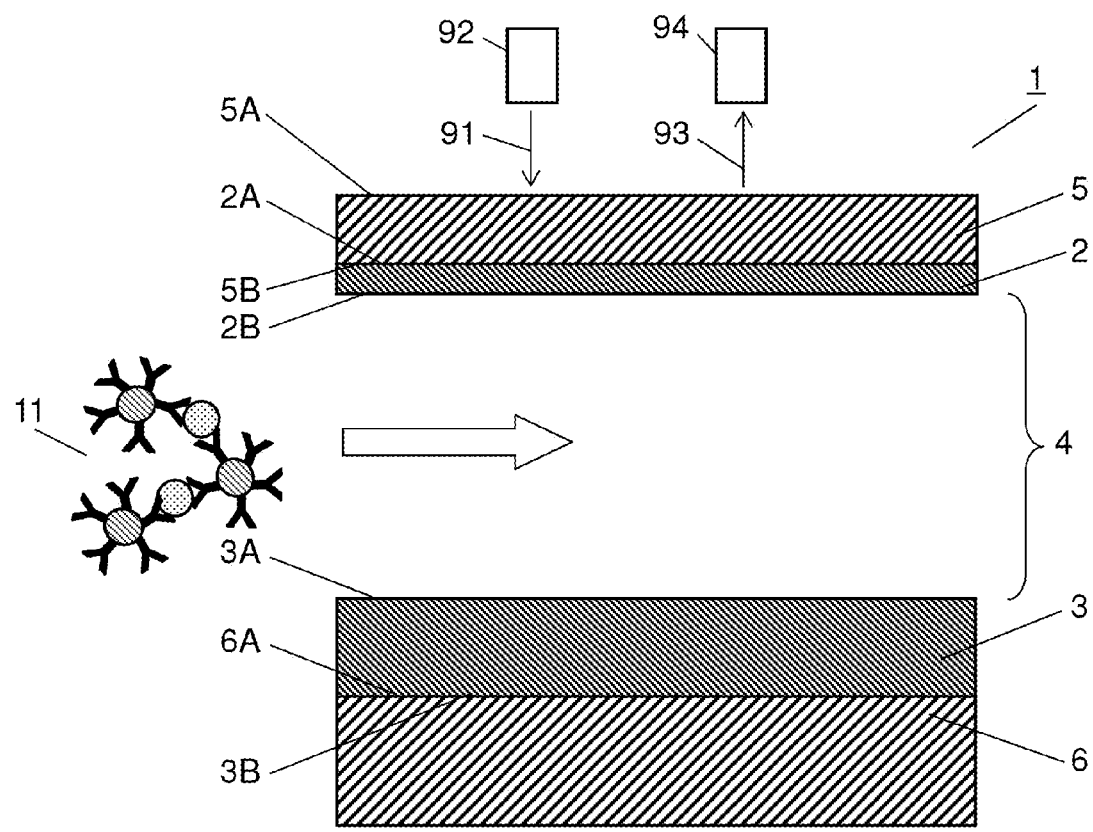
FIG. 12 is a side sectional view of the sensor device in accordance with Embodiment 1.

According to Embodiment 1, analytes 8 are specifically bound with acceptors 7 of carriers 10 in flow path 4. FIG. 12 is a side sectional view of sensor device 1 in which analytes 8 are specifically bound with carriers 10 outside flow path 4 to form aggregates 11 before analytes 8 and carriers 10 flow into region 18. Aggregates 11 are then input in flow path 4. In this case, aggregates 11 can be formed, e.g. before aggregates 11 are input into sensor device 1, or analytes 8 and carriers 10 are specifically bound together in reservoir 25 for forming aggregates 11. Sensor device 1 shown in FIG. 12 allows analytes 8 and carriers 10 to be specifically bound together without fail, hence increasing detection accuracy. Acceptors 7 chemically adsorbed to metal layers 2 and 3 shown in FIG. 8A can be disposed in sensor device 1 shown FIG. 12, and aggregates 11 can be trapped and fixed to concentrate locally at region 18 (aggregate trapping section).

Exemplary Embodiment 2

Figure 13A:
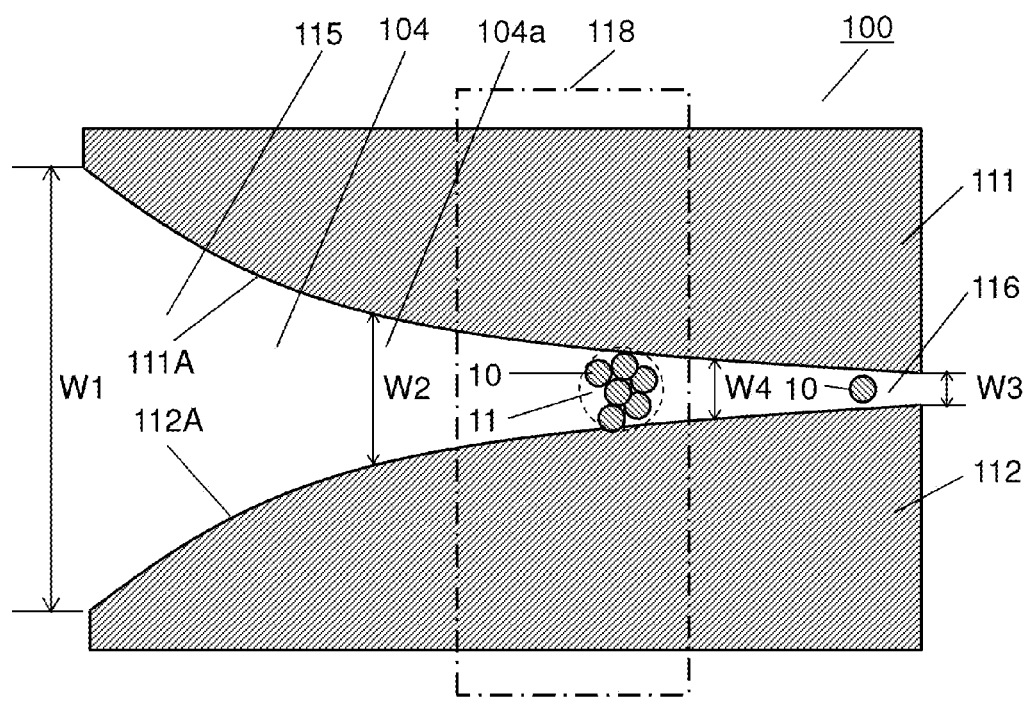
FIG. 13A is a top sectional view of a sensor device in accordance with Exemplary Embodiment 2 of the present disclosure.
Figure 13B:
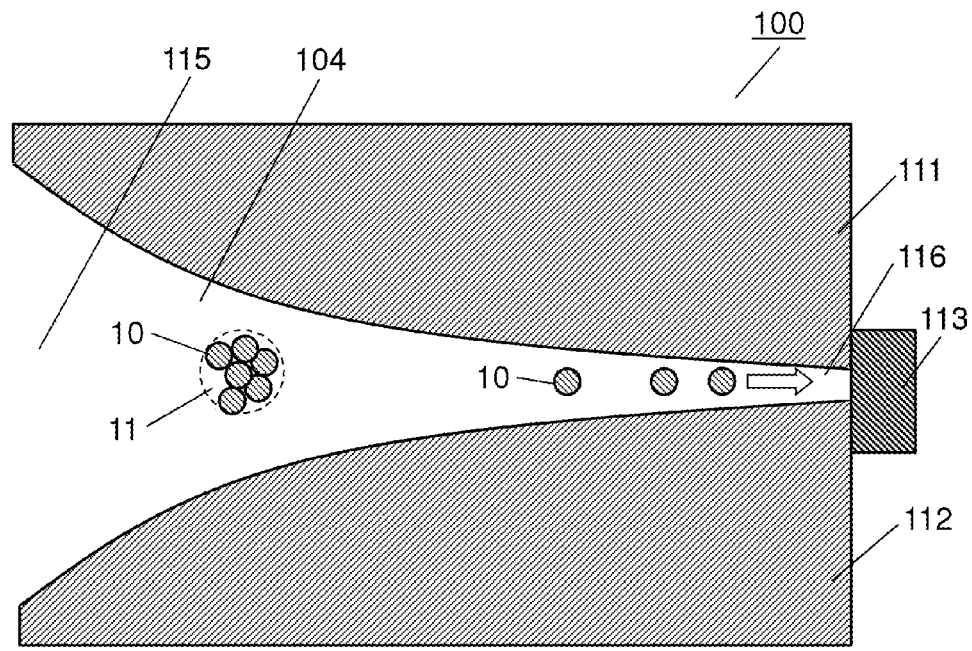
FIG. 13B is a top sectional view of another sensor device in accordance with Embodiment 2.
Figure 14A:
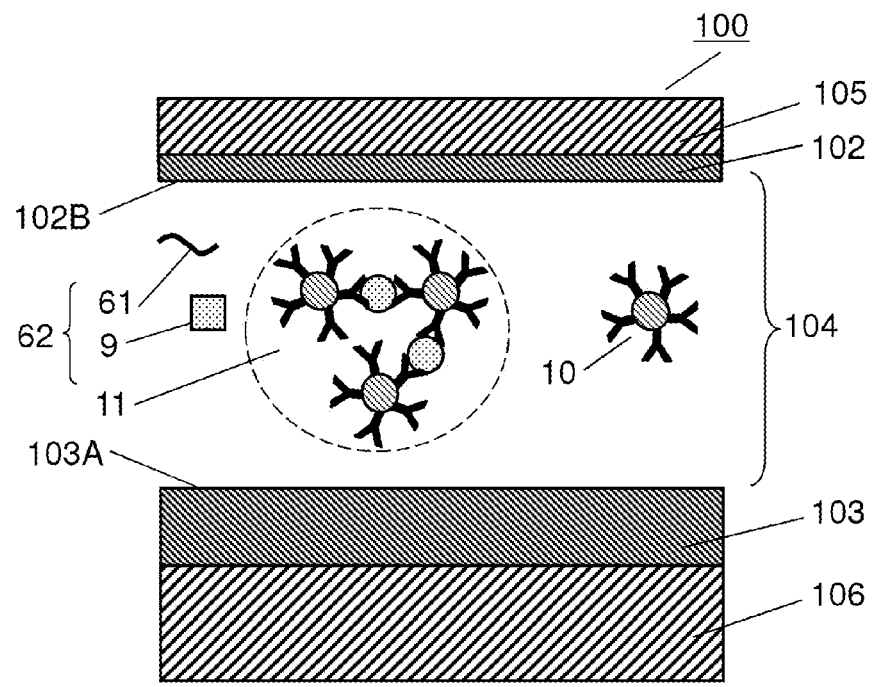
FIG. 14A is a side sectional view of the sensor device in accordance with Embodiment 2.
Figure 14B:
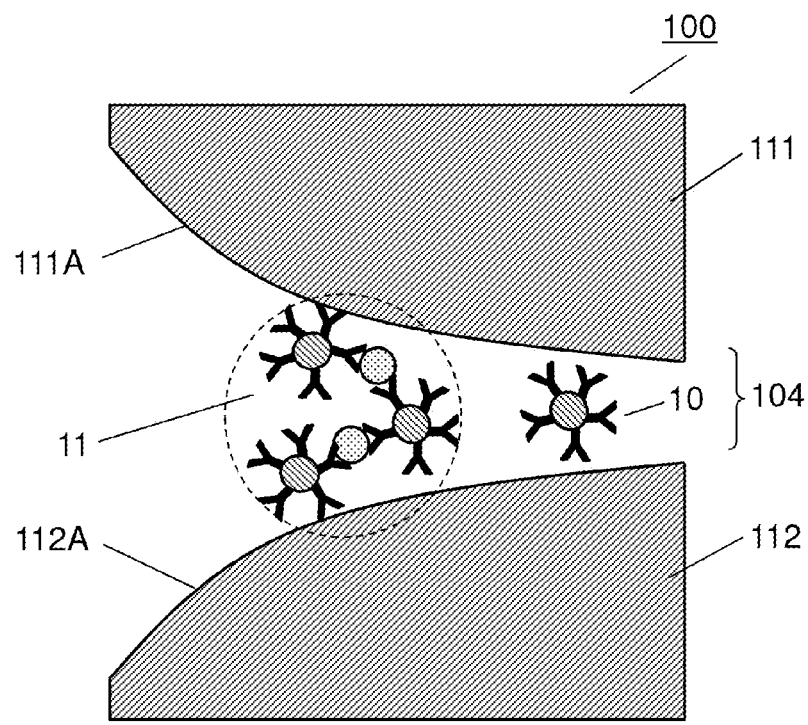
FIG. 14B is a top sectional view of the sensor device shown in FIG. 14A.

FIGS. 13A and 13B are top sectional views of sensor device 100 in accordance with Exemplary Embodiment 2. In FIGS. 13A and 13B, components identical to those of sensor device 1 according to Embodiment 1 are denoted by the same reference numerals. A side sectional view of sensor device 100 in accordance with Embodiment 2 is the same as that of sensor device 1 shown in FIG. 1B. FIGS. 14A and 14B are a side sectional view and a top sectional view of sensor device 100, respectively. Sensor device 100 includes flow path 104 surrounded by four surfaces, namely, lower surface 102B of metal layer 102, upper surface 103A of metal layer 103, side surface 111A of side wall 111, and side surface 112A of side wall 112. Lower surface 102B of metal layer 102 constitutes an upper surface of flow path 104, and upper surface 103A of metal layer 103 constitutes a lower surface of flow path 104. Side surface 111A of side wall 111 constitutes a first side surface, and side surface 112A of side wall 112 constitutes a second side surface of flow path 104. Flow path 104 includes input region 115 configures to allow sample 62 to be input thereto, and discharge region 116 configured to allow sample 62 to be discharged. Flow path 104 tapers from input region 115 to discharge region 116, namely, the interval between side surface 111A and side surface 112A decreases gradually from input region 115 toward discharge region 116. A front tip (the left end in FIG. 13) of input region 115 has a width W1, a tail end (the right end in FIG. 13) of discharge region 116 has a width W3, and arbitrary position 104a in flow path 104 has a width W2. Flow path 104 is configured such that these widths satisfy the relation of W1≥W2≥W3. Sample 62 is input into flow path 104, and then, analytes 8 in sample 62 and acceptors 7 of carriers 10 are specifically bound together and form aggregates 11. As sample 62 flows from input region 115 to discharge region 116, aggregates 11 move from input region 115 toward discharge region 116. Width W4 of discharge region 116 is larger than a diameter of carrier 10 and is smaller than a diameter of aggregate 11. In other words, width W4 of discharge region 116 is larger than a first predetermined value not smaller than the diameter of carrier 10, while width W4 is not larger than a second predetermined value that is smaller than the diameter of aggregate 11.

In flow path 104, aggregates 11 are trapped at specific region 118 between input region 115 and discharge region 116. Region 118 thus functions as an aggregate trapping section. Aggregate 11 trapped at region 118 block flow path 104, so that other aggregates 11 coming next is stopped by the trapped aggregate 11. As a result, aggregates 11 are accumulated together at specific region 118. To be more specific, carrier 10 in sample 62 having a diameter not larger than the first predetermined value, non-specific specimen 9 having a diameter smaller than that of carrier 10, and medium 61 can pass through region 118. However, aggregate 11 in sample 62 and having a diameter larger than the second predetermined value cannot pass through region 118.

Figure 15:
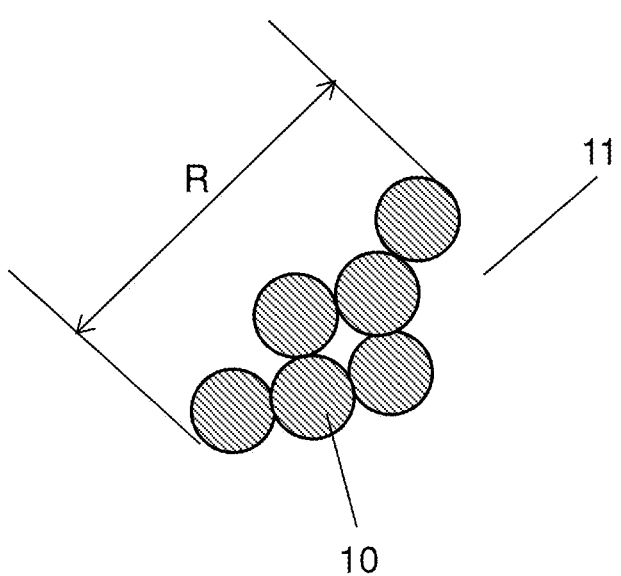
FIG. 15 schematically illustrates an aggregate.

FIG. 15 is a schematic view of aggregate 11. Aggregate 11 includes plural carriers 10 bound with each other via an analyte. Aggregate 11 may have various shapes. According to this embodiment, the diameter of aggregate 11 refers to maximum diameter R of aggregate 11 as shown in FIG. 15. In other words, the second predetermined value is smaller than maximum diameter R.

As discussed above, sensor device 100 in accordance with Embodiment 2 traps aggregates 11 containing analytes 8 at specific region 118 of flow path 104, so that the dielectric constant at region 118 may change more significantly than at other regions. A status of the electromagnetic wave (e.g. color of visible light) propagating upward form metal layer 102 contacting region 118 of flow path 104 is different from that of the electromagnetic wave propagating upward from metal layer 102 contacting regions of the flow path other than region 118. This operation allows a user at home to visibly recognize presence of anayltes easily. In other words, sensor device 100 in accordance with Embodiment 2 has higher detection sensitivity than a sensor device in which aggregates 11 are not trapped but are uniformly distributed in flow path 104.

Sample 62 flows from input region 115 to discharge region 116 to cause aggregates 11 to be trapped at the specific region in flow path 104. Sensor device 100 shown in FIG. 13B includes absorber 113 near discharge region 116 of flow path 104 for absorbing sample 62. The absorption of sample 62 into absorber 113 causes sample 62 to flow from input region 115 to discharge region 116, so that aggregates 11 and carriers 10 can flow toward discharge region 116. Aggregates 11 are then trapped at region 118, and carriers 10 are discharged from discharge region 116 to the outside of flow path 104. Absorber 113 shown in FIG. 13B is added to sensor device 100 shown in FIG. 13A. Absorber 113 can be used also in sensor devices other than sensor device 100 shown in FIG. 13A for enlarging the flow of the samples in flow paths 4 and 104 similarly to sensor device 100 shown in FIG. 13B.

In sensor device 100 shown in FIG. 13A, width W2 of flow path 104 decreases continuously from the front tip of input region 115 to the tail end of discharge region 116. Width W2 may decrease discontinuously from the front tip of input region 115 to the tail end of discharge region 116. The width of region 118 may decrease continuously. The width of at least one of input region 115 and discharge region 116 can be constant.

Exemplary Embodiment 3

Figure 16A:
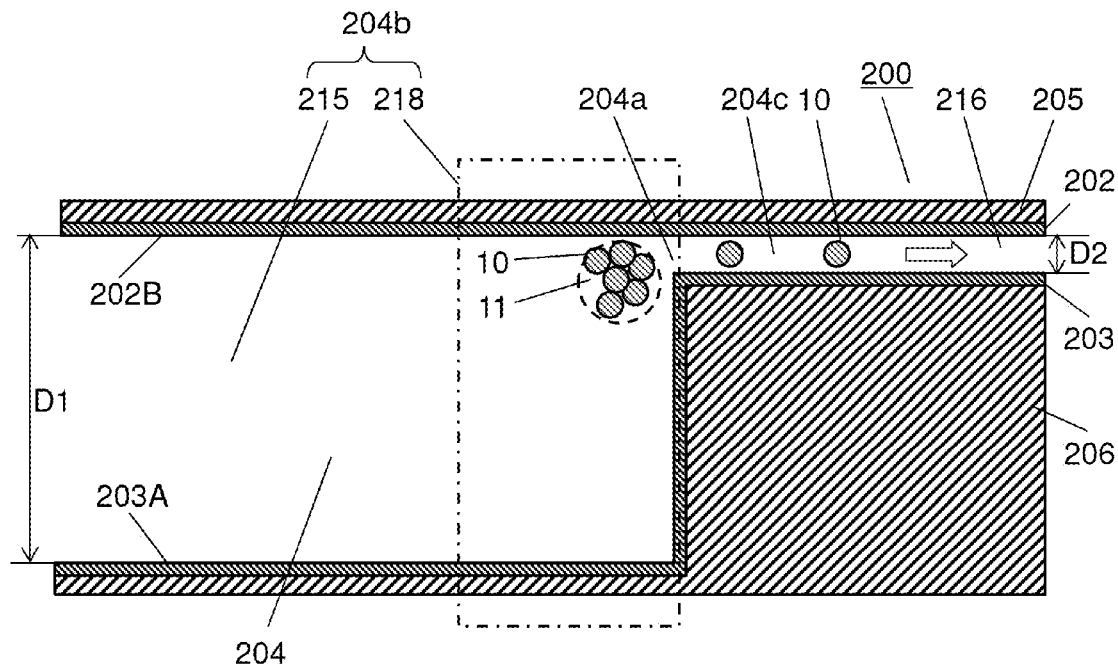
FIG. 16A is a side sectional view of a sensor device in accordance with Exemplary Embodiment 3 of the present disclosure.
Figure 16B:
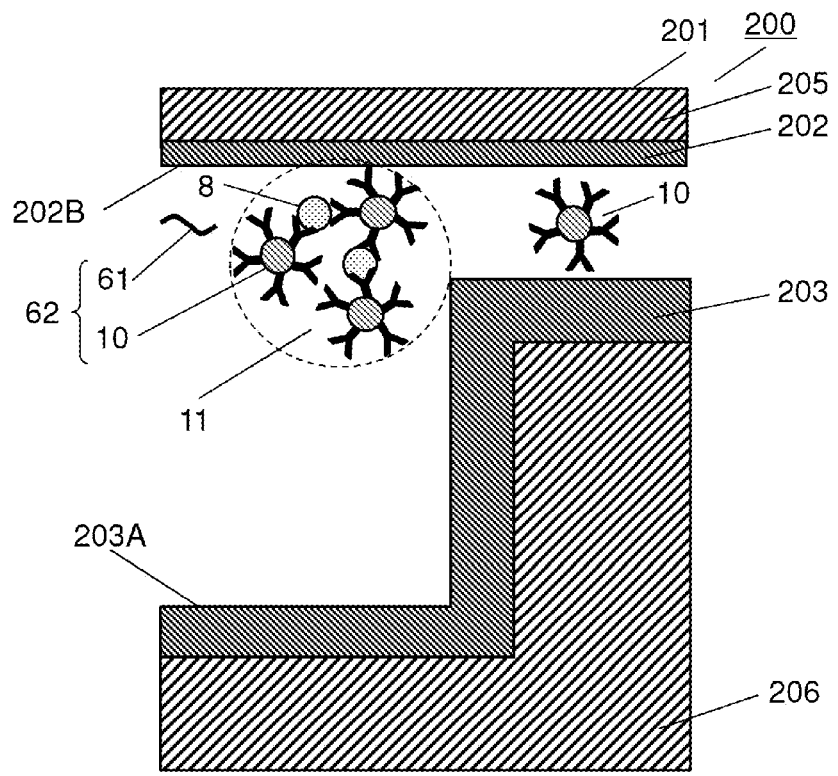
FIG. 16B is an enlarged view of the sensor device shown in FIG. 16A.

FIGS. 16A and 16B are a side sectional view and an enlarged side sectional view of sensor device 200 in accordance with Exemplary Embodiment 3, respectively. A top view of sensor device 200 is the same as that of sensor device 1 in accordance with Embodiment 1 shown in FIG. 1A. As shown in FIG. 16A, sensor device 200 includes flow path 204 constituted by four surfaces surrounding flow path 204, namely, two side surfaces of two side walls similar to side walls 21 and 22 according to Embodiment 1, lower surface 202B of metal layer 202, and upper surface 203A of metal layer 203. The two side surfaces constitute first and second side surfaces of flow path 204, lower surface 202B of metal layer 202 constitutes an upper surface of flow path 204, and upper surface 203A of metal layer 203 constitutes a lower surface of flow path 204. Flow path 204 includes input region 215 configures to allow sample 62 to be input thereto, discharge region 216 configures to allow sample 62 discharged, and region 218 disposed between input region 215 and discharge region 216. Region 218 functions as an aggregate trapping section. Flow path 204 includes flow path 204b (first flow path) and flow path 204c (second flow path). Flow path 204b includes input region 215 and region 218 (aggregate trapping section). Flow path 204c includes discharge region 216. An interval between lower surface 202B and upper surface 203A is referred to as a depth of flow path 204. A depth of flow path 204b is denoted by D1 and the depth of flow path 204c is denoted by D2. Depth D1 is an interval between lower surface 202B of metal layer 202 and upper surface 203A of metal layer 203 in flow path 204b, and depth D2 is an interval between them in flow path 204c. Flow path 204 is configured such that intervals D1 and D2 satisfy the relation of D1>D2. Upon sample 62 being input into flow path 204, analytes 8 in sample 62 are specifically bound with acceptors 7 of carriers 10 to form aggregates 11. Following the flow of sample 62 from input region 215 to discharge region 216, aggregates 11 thus move toward discharge region 216.

The depth (interval D2) of flow path 204c is larger than the diameter of carrier 10 and smaller than the diameter of aggregate 11. To be more specific, the depth (interval D2) of flow path 204c is larger than a first predetermined value that is not smaller than the diameter of carrier 10 and that is not larger than a second predetermined value that is smaller than the diameter of aggregate 11.

In flow path 204, aggregate 11 is trapped at specific region 218 of flow path 204, and then, aggregates 11 coming next are tacked together at specific region 218 since the trapped aggregate 11 blocks the flow path. FIG. 16B is an enlarged view of region 218 at which aggregate 11 is trapped. Carriers 10 in sample 62 and having a diameter not larger than the first predetermined value, non-specific specimen 9 having a diameter smaller than that of carrier 10, and medium 61 can pass through region 218. However, aggregate 11 having a diameter larger than the second predetermined value cannot pass through region 218.

Sensor device 200 in accordance with Embodiment 3 traps aggregates 11 containing analytes 8 at specific region 218 of flow path 204, so that the dielectric constant of region 218 may change significantly larger than the dielectric constant of other regions. A status of the electromagnetic wave (e.g. color of the visible light) propagating upward form metal layer 202 contacting region 218 of flow path 204 changes, and a status of the electromagnetic wave (e.g. color of the visible light) propagating upward from metal layer 202 contacting the regions other than region 218 also changes. These phenomena allow a user at home to easily recognize visibly the presence of analytes. In other words, sensor device 200 has higher detection sensitivity than a sensor device in which aggregates 11 are not trapped but are uniformly distributed in the flow path.

An absorber may be disposed near discharge region 216 to form a flow of sample 62 in flow path 204 similarly to the absorber according to Embodiment 2. The absorber allows sample 62 to flow from input region 215 toward discharge region 216 of flow path 204, so that aggregates 11 and carriers 10 may flow toward discharge region 216. As a result, aggregates 11 are trapped at region 218, and carriers 10 are discharged from discharge region 216 to the outside of flow path 204.

Figure 17:
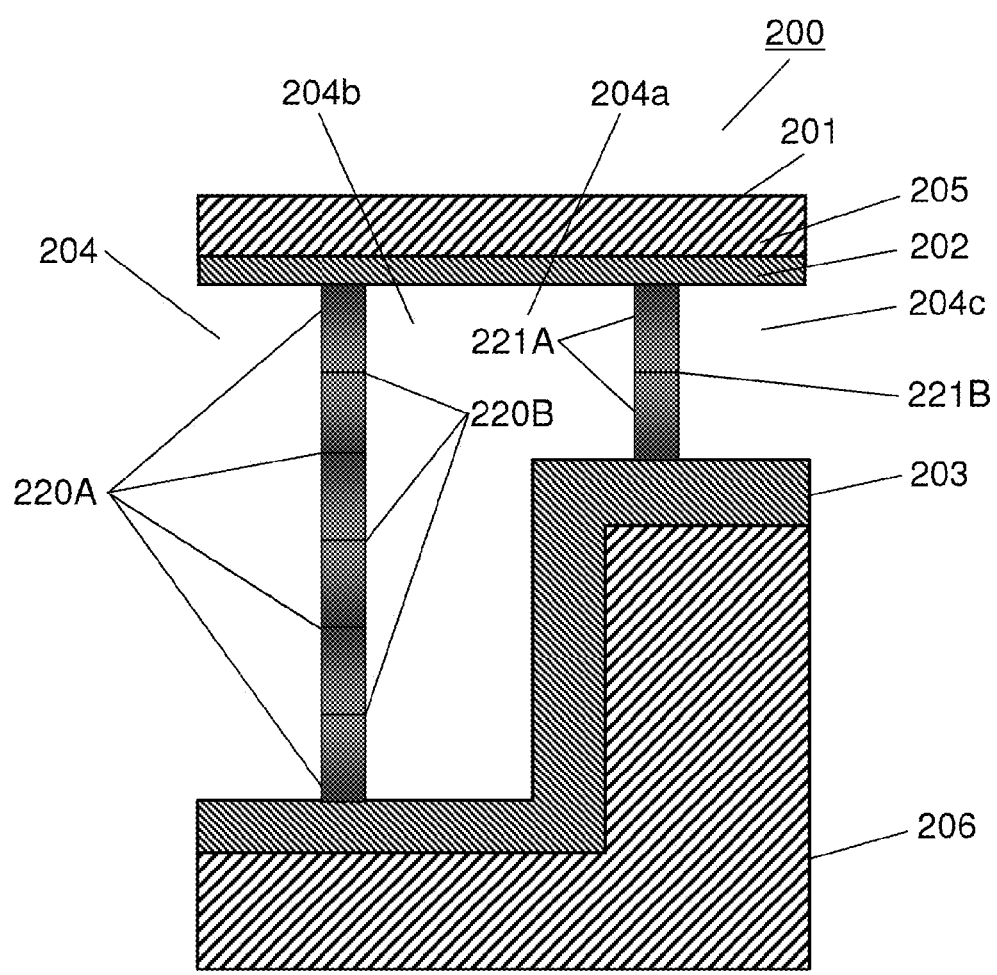
FIG. 17 shows a distribution of electromagnetic intensity of the sensor device in accordance with Embodiment 3.

FIG. 17 shows a distribution of electromagnetic field intensity in sensor device 200 in accordance with Embodiment 3. As shown in FIG. 17, an interference state between the electromagnetic waves propagating upward from metal layer 202 contacting flow path 204b can be almost identical to an interference state between the electromagnetic waves propagating upward from metal layer 202 contacting flow path 204c. To be more specific, flow path 204b and flow path 204c are configured such that these two paths satisfy formula 1 or formula 2. Note that integer m in formulae (1) and (2) is different from flow path 204b and flow path 204c. In other words, interval D1 between the upper surface and lower surface of flow path 204b and interval D2 between the upper surface and the lower surface of flow path 204c satisfy one of relations (a) or (b) with integers m1 and m2, a wavelength λ of the electromagnetic wave in vacuum, a refraction index n in flow path 204, and an incident angle θ of the electromagnetic wave:

$$(m1+\tfrac{1}{2}) \times \lambda = 2 \times n \times D1 \times \cos\theta, \text{ and } (m2+\tfrac{1}{2}) \times \lambda = 2 \times n \times D2 \times \cos\theta \qquad (a)$$

$$m1 \times \lambda = 2 \times n \times D1 \times \cos\theta, \text{ and } m2 \times \lambda = 2 \times n \times D2 \times \cos\theta \qquad (b)$$

When light in a visible light band is supplied from above metal layer 202 of sensor device 200, the condition discussed above allows the color of the light reflected on the region contacting flow path 204b of metal layer 202 and the color of the light reflected on the region contacting flow path 204c of metal layer 202 to be almost equal to each other. Therefore, analytes 8 and acceptors 7 of carriers 10 are specifically bound together to form aggregates 11. Aggregates 11 are then trapped and stacked at aggregate trapping section 218 (region 218). Then, the light reflected on the region contacting aggregate trapping section 218 of metal layer 202 changes remarkably, so that a user at home can visibly recognize the presence of analytes easily with this sensor device 200.

Sensor device 200 allows the user to detect a change in color for detecting the presence of analytes, so that the light source preferably employs a light source of a visible light band. The visible light band refers to a wavelength band containing light visible by human eyes. This wavelength band is not smaller than 380 nm and not larger than 750 nm. For instance, sensor device 200 is configured such that the visible light band (i.e. colors of orange or red) having a wavelength ranging from 580 nm to 600 nm satisfies formula 2 when sample 62 not containing analytes 8 has been input in flow path 204. Then, a sample containing analytes 8 is input into flow path 204. This causes a change in refraction index (dielectric constant) of the aggregate trapping section 218 (region 218). The material for the carriers can be selected appropriately, or a structure of aggregate trapping section 218 can be determined such that the light reflected on the region contacting aggregate trapping section 218 of metal layer 202 and having a wavelength not larger than 560 nm can satisfy formula 2. The above arrangement allow the specific binding to change the wavelength of the reflected light between a band shorter than the wavelength of yellow (about 560-580 nm) that shows a significant color difference for human eyes and a band larger than the wavelength. As a result, a user at home can visibly recognize the presence of the specific binding easily.

A filter allowing only a predetermined wavelength to pass through the filter may be disposed between sensor device 200 and human eyes of a user who observes sensor device 200. In this case, a filter that blocks the wavelength shorter than 580 nm is disposed, then this filter allows the light having a wavelength not smaller than 580 nm to pass through when sample 62 contains no analytes, so that sensor device 200 looks bright to the user; however, when sample 62 contains analytes, the filter causes the wavelength that satisfies formula 2 to attenuate to cause sensor device 200 to look dark. A brightness change may be recognized more easily than a color change, so that the foregoing structure may be effective.

Exemplary Embodiment 4

Figure 18A:
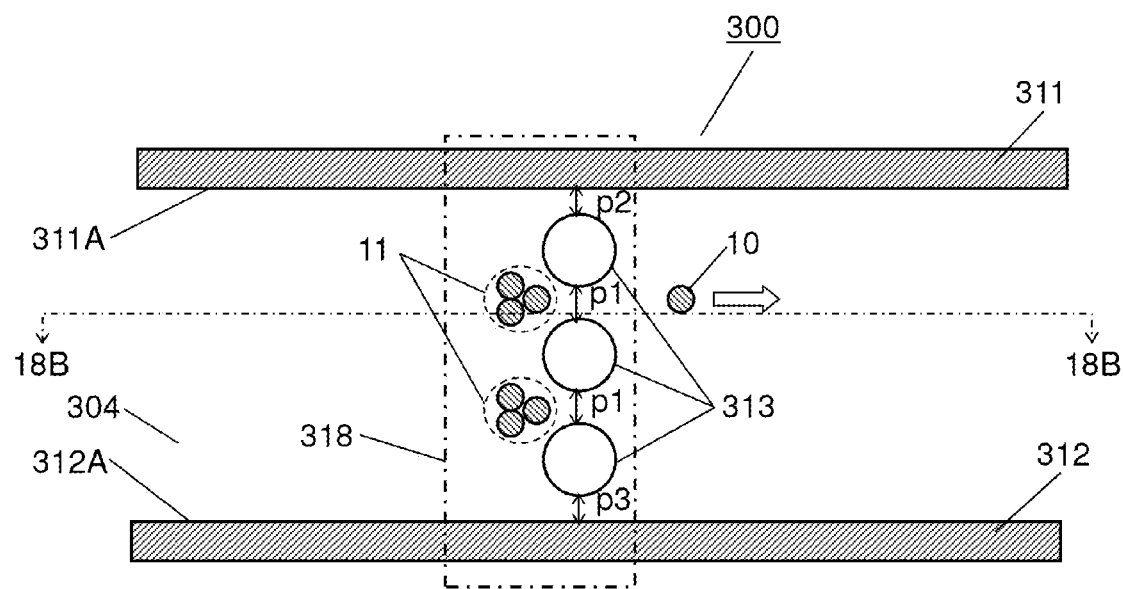
FIG. 18A is a top sectional view of a sensor device in accordance with Exemplary Embodiment 4 of the present disclosure.
Figure 18B:
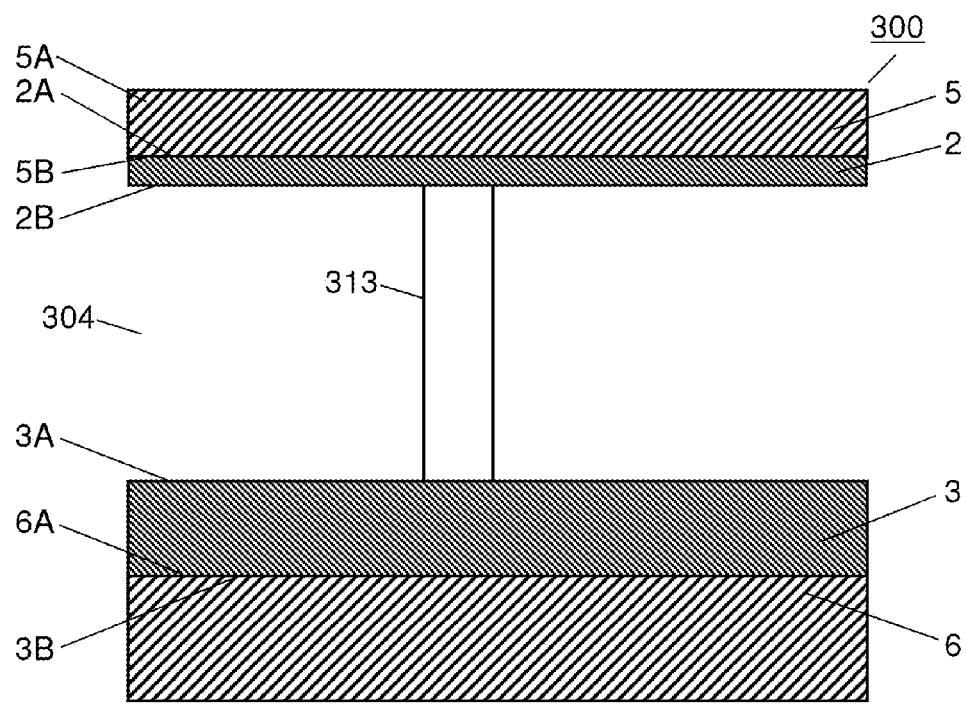
FIG. 18B is a side sectional view of the sensor device at line 18B-18B shown in FIG. 18A.

FIG. 18A is a top sectional view of sensor device 300 in accordance with Exemplary Embodiment 4. FIG. 18B is a side sectional view of sensor device 300 at line 18B-18B shown in FIG. 18A. In FIGS. 18A and 18B, components identical to those of sensor device 1 shown in FIGS. 2A and 2B in accordance with Embodiment 1 are denoted by the same reference numerals. Sensor device 300 includes flow path 304 constituted by four surfaces surrounding flow path 304: side surface 311A of side wall 311, side surface 312A of side wall 312, lower surface 2B of metal layer 2, and upper surface 3A of metal layer 3. Side surface 311A of side wall 311 constitutes a first side surface of flow path 304. Side surface 312A of side wall 312 constitutes a second side surface of flow path 304. Lower surface 2B of metal layer 2 constitutes an upper surface of flow path 304. Upper surface 3A of metal layer 3 constitutes a lower surface of flow path 304. Sensor device 300 includes plural pillars 313 extending in parallel to side surfaces 311A and 312A from lower surface 2B of metal layer 2 to upper surface 3A of metal layer 3. Plural pillars 313 are disposed at specific region 318 of flow path 304, and have a cylindrical shape according to Embodiment 4; however pillars 313 can have another shape. Interval p1 between pillars 313 adjacent to each other, interval p2 between side wall 311 and pillar 313, and interval p3 between side wall 312 and pillar 311 are determined such that carrier 10 can pass through between pillars 313 and side walls 311, 312; however, aggregates 11 can be trapped there. Interval p1 is a distance between outer walls of two adjacent pillars 313. Interval p2 is a distance between side wall 311A of side wall 311 and the outer wall of pillar 313. Interval p3 is a distance between side wall 312A of side wall 312 and the outer wall of pillar 313. Intervals p1, p2, and p3 are larger than a diameter of carrier 10, and smaller than a diameter of aggregate 11. To be more specific, intervals p1, p2, and p3 are larger than a first predetermined value not smaller than the diameter of carrier 10, and is not larger than a second predetermined value smaller than the diameter of aggregate 11. As discussed above, region 318 of flow path 304 functions as an aggregate trapping section for trapping aggregates 11. The sample crosses pillars 313 perpendicularly to pillars 313 in flow path 304; however, pillars 313 can slant toward the flow of the sample while they keep intersecting with the flow at right angles, namely pillars 313 can extend slantingly at a predetermined angle from side walls 311 and 312.

Figure 18C:
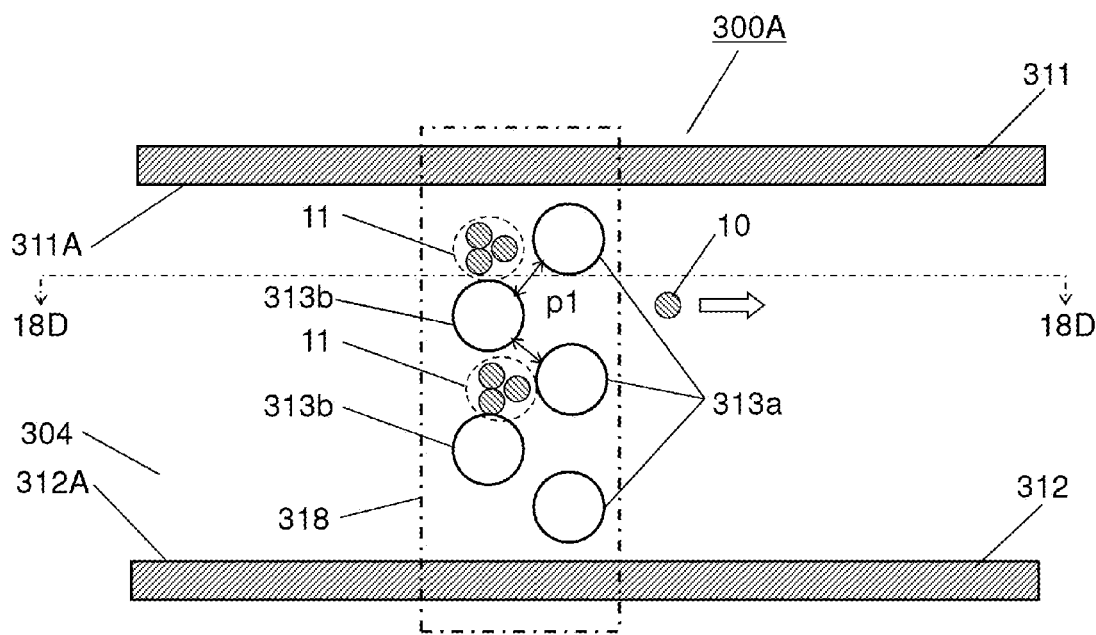
FIG. 18C is a top sectional view of another sensor device in accordance with Embodiment 4.
Figure 18D:
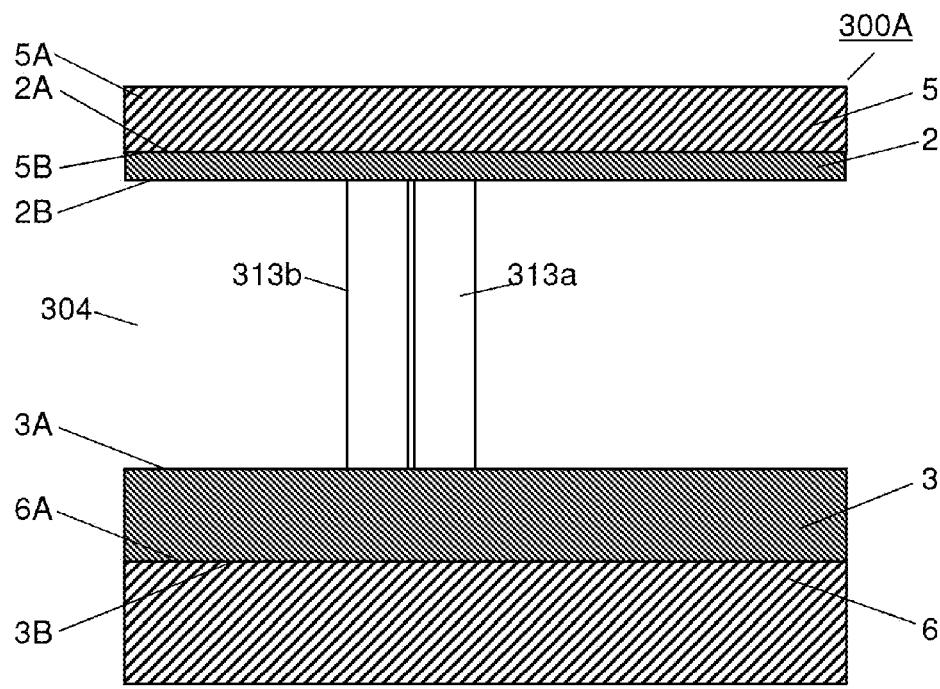
FIG. 18D is a side sectional view of the sensor device at line 18D-18D shown in FIG. 18C.

FIG. 18C is a top sectional view of another sensor device 300A in accordance with Embodiment 4. FIG. 18D is a side sectional view of sensor device 300A at line 18D-18D shown in FIG. 18C. In FIGS. 18C and 18D, components identical to those of sensor device 300 shown in FIGS. 18A and 18B are denoted by the same reference numerals. Sensor device 300A includes plural pillars 313a and 313b instead of pillars 313 of sensor device 300. Pillars 313a and 313b extend in parallel to side surfaces 311A and 312A from lower surface 2B of metal layer 2 to upper surface 3A of metal layer 3. Plural pillars 313a and 313b are disposed at specific region 318 of flow path 304, and have a cylindrical shape according to Embodiment 4; however may have another shape. Pillars 313a and 313b are arranged alternately on two lines. An interval between adjacent pillars 313a and 313b, an interval between pillar 313a and side surface 311A, and an interval between pillar 313a and side surface 312A are determined such that carriers 10 can pass through the intervals between pillars 313a, 313b and side wall 311, 312, but aggregates 11 are trapped at these intervals. Plural pillars 313a and 313b may be arranged on three or more lines.

Multiple pillars 313 can be connected to side surface 311A and 312A instead of surfaces 2B and 3B of metal layers 2 and 3, and can extend in parallel to surfaces 2B and 3B. In this case, an interval between pillars 313 adjacent to each other, and an interval between pillar 313 and upper surface 3A of metal layer 3, and an interval between pillar 313 and lower surface 2B of metal layer 2 are determined such that carriers 10 can pass through the intervals between pillars 313 and metal layers 2 and 3; however, aggregates 11 can be trapped there.

As discussed above, sensor devices 300 and 300A in accordance with Embodiment 4 allow specific region 318 of flow path 304 to trap aggregates 11 containing analytes 8, so that the dielectric constant at region 318 can change more remarkably than other regions. These changes cause a change in a state of electromagnetic wave (e.g. color of visible light) propagating upward from metal layer 2 contacting region 318 as well as in a state of electromagnetic wave (e.g. color of visible light) propagating upward from metal layer 2 contacting other regions. A user at home thus can recognize the presence of analytes easily. In other words, sensor devices 300 and 300A can have high detection sensitivity to analytes than a sensor device in which aggregates are not trapped but are distributed uniformly in a flow path.

In FIGS. 18A to 18D, the intervals between pillars 313, 313a, and 313b adjacent to each other can be different from each other.

Exemplary Embodiment 5

Figure 19A:
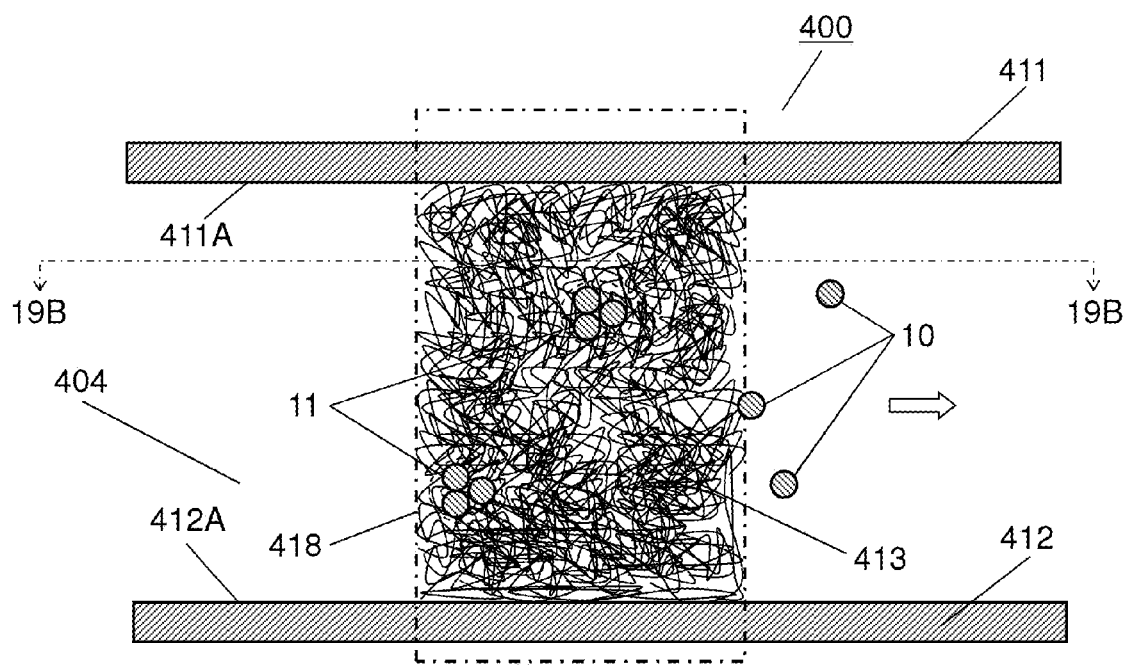
FIG. 19A is a top sectional view of a sensor device in accordance with Exemplary Embodiment 5 of the present disclosure.
Figure 19B:
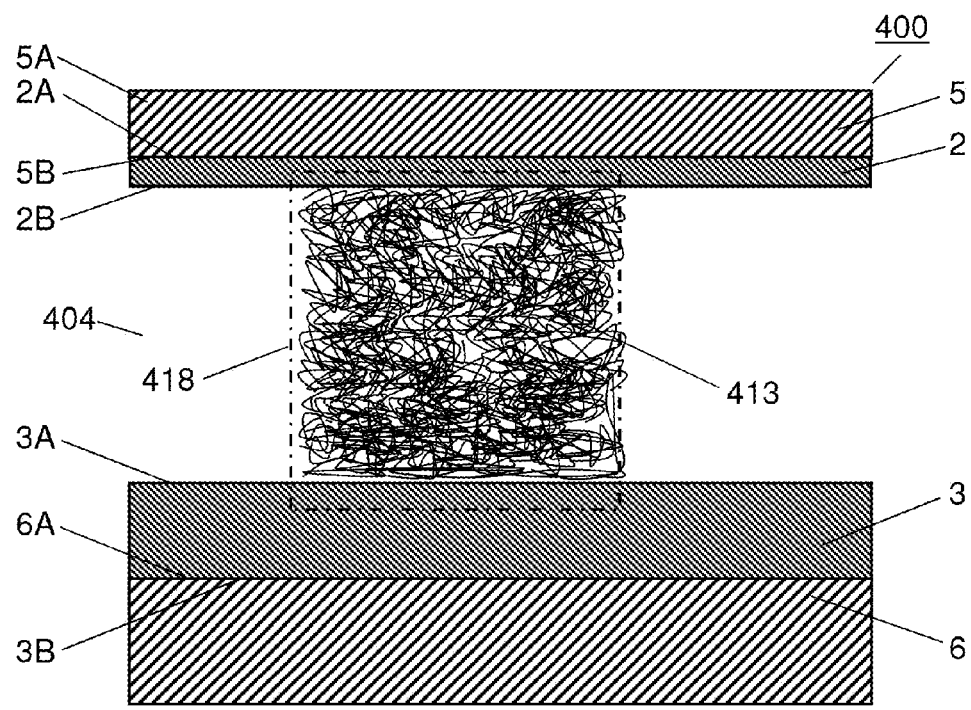
FIG. 19B is a side sectional view of the sensor device at line 19B-19B shown in FIG. 19A.

FIG. 19A is a top sectional view of sensor device 400 in accordance with Exemplary Embodiment 5. FIG. 19B is a side sectional view of sensor device 400 at line 19B-19B shown in FIG. 19A. In FIGS. 19A and 19B, components identical to those of sensor device 1 shown in FIGS. 2A and 2B in accordance with Embodiment 1 are denoted by the same reference numerals. Sensor device 400 includes flow path 404 constituted by four surfaces surrounding path 404: side surface 411A of side wall 411, side surface 412A of side wall 412, lower surface 2B of metal layer 2, and upper surface 3A of metal layer 3. Side surface 411A of side wall 411 constitutes a first side surface of flow path 404. Side surface 412A of side wall 412 constitutes a second side surface of flow path 404. Lower surface 2B of metal layer 2 constitutes an upper surface of flow path 404. Upper surface 3A of metal layer 3 constitutes a lower surface of flow path 404. Sensor device 400 includes plural fibrous substances 413 disposed at specific region 418 of flow path 404. Fibrous substances 413 tangle with each other and form a mesh having apertures. The minimum value of aperture widths of the mesh is determined such that carrier 10 can pass through the apertures but aggregate 11 cannot pass through the apertures. In other words, the minimum diameter of the apertures is larger than a diameter of carrier 10 and smaller than a diameter of aggregate 11. To be more specific, the minimum diameter of the aperture is larger than a first predetermined value not smaller than the diameter of carrier 10, and is not larger than a second predetermined value smaller than the diameter of aggregate 11. The mesh structure having the apertures and formed of tangled fibrous substances 413 is disposed at specific region 418 of flow path 404.

The foregoing structure traps aggregates 11, as a result of filtration, having a diameter larger than the minimum diameter of the apertures among fibrous substances 413. On the other hand, carriers 10 having a diameter smaller than the minimum diameter of the apertures pass through fibrous substances 413. Region 418 thus functions as an aggregate trapping section for trapping aggregates 11. Fibrous substances 413 having the mesh structure may be made of silicon dioxide nano-fiber.

Sensor device 400 in accordance with Embodiment 5 allows specific region 418 of flow path 404 to trap aggregates 11 containing analytes 8, so that the dielectric constant of region 418 changes more remarkably than other regions. These changes cause a change in state of electromagnetic wave (e.g. color of visible light) propagating upward from metal layer 2 contacting region 418 as well as in state of electromagnetic wave (e.g. color of visible light) propagating upward from metal layer 2 contacting other regions. A user at home thus can recognize the presence of analytes easily. In other words, sensor device 400 can have higher detection sensitivity to analytes than a sensor device in which aggregates are not trapped but distributed uniformly in a flow path.

Exemplary Embodiment 6

Figure 20A:
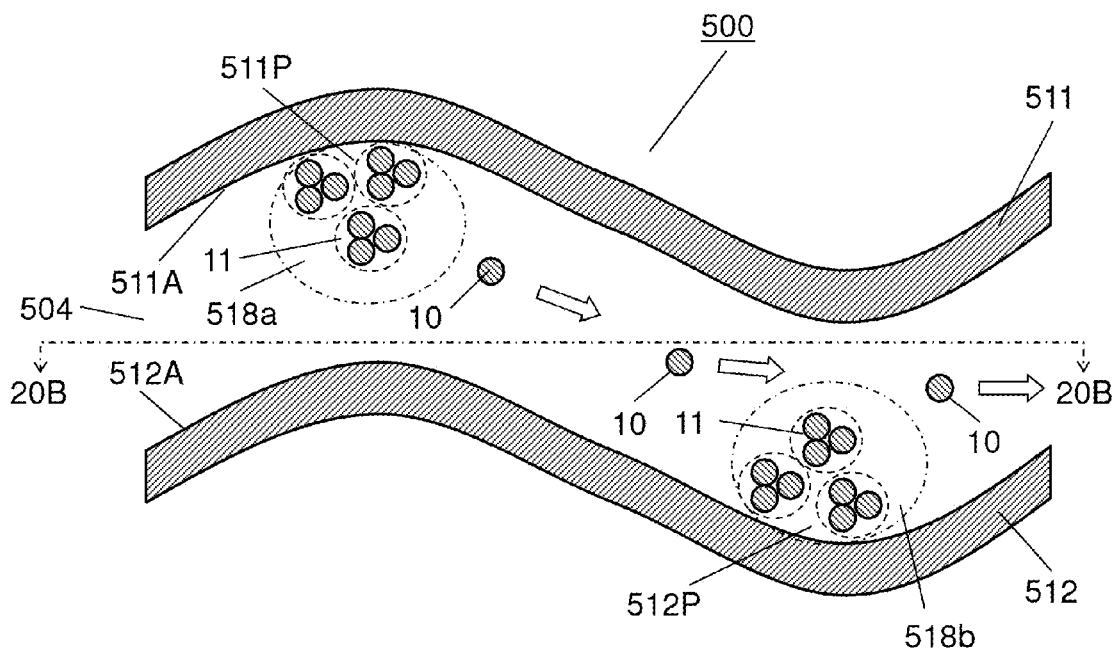
FIG. 20A is a top sectional view of a sensor device in accordance with Exemplary Embodiment 6 of the present disclosure.
Figure 20B:
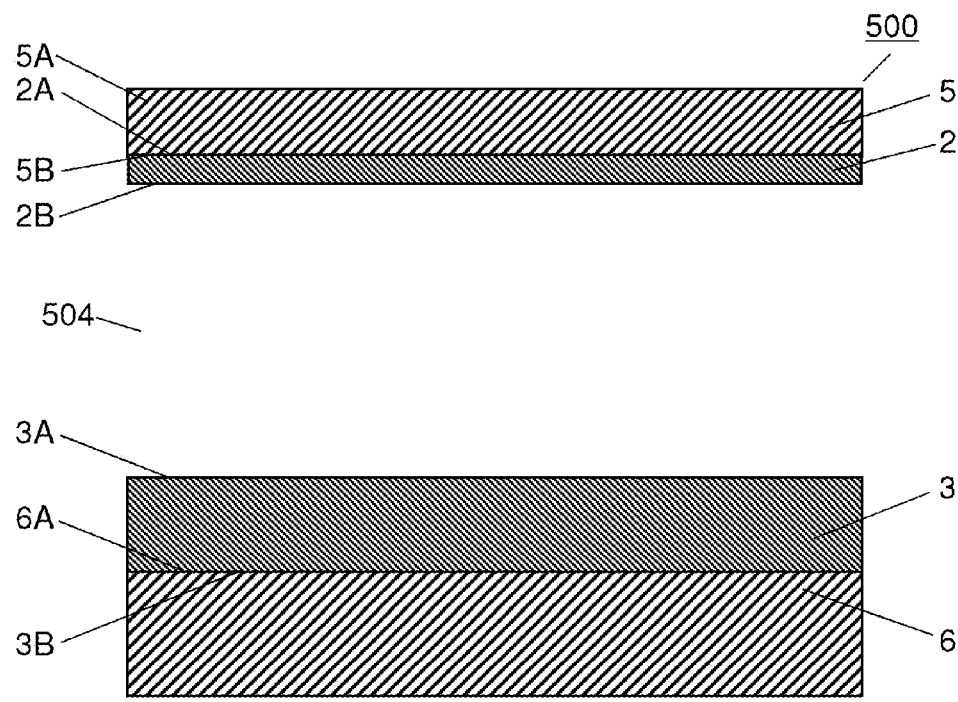
FIG. 20B is a side sectional view of the sensor device at line 20B-20B shown in FIG. 20A.

FIG. 20A is a top sectional view of sensor device 500 in accordance with Exemplary Embodiment 6. FIG. 20B is a side sectional view of sensor device 500 at line 20B-20B shown in FIG. 20A. In FIGS. 20A and 20B, components identical to those of sensor device 1 shown in FIGS. 2A and 2B in accordance with Embodiment 1 are denoted by the same reference numerals. Sensor device 500 includes flow path 504 constituted by four surfaces surrounding flow path 504: side surface 511A of side wall 511, side surface 512A of side wall 512, lower surface 2B of metal layer 2, and upper surface 3A of metal layer 3. Side surface 511A of side wall 511 constitutes a first side surface of flow path 504. Side surface 512A of side wall 512 constitutes a second side surface of flow path 504. Lower surface 2B of metal layer 2 constitutes an upper surface of flow path 504. Upper surface 3A of metal layer 3 constitutes a lower surface of flow path 504. Side surfaces 511A and 512A of flow path 504 meander such that recesses 511P and 512P are formed at specific regions 518a and 518b. While sample 62 flows through flow path 504, aggregates 11 are trapped in recesses 511p and 512p formed at specific regions 518a and 518b which function as aggregate trapping sections for trapping aggregates 11. Flow path 504 can meander such that one of side surface 511A or 512A can have a recess therein.

Sensor device 500 in accordance with Embodiment 6 allows specific region 518 of flow path 504 to trap aggregates 11 containing analytes 8, so that the dielectric constant of region 518 changes more remarkably than other regions. These changes cause a change in a state of electromagnetic wave (e.g. color of visible light) propagating upward from metal layer 2 contacting regions 518a and 518b as well as in a state of electromagnetic wave (e.g. color of visible light) propagating upward from metal layer 2 contacting other regions. A user at home thus can recognize the presence of analytes easily. In other words, sensor devices 500 can have higher detection sensitivity to analytes than a sensor device in which aggregates are not trapped but are distributed uniformly in a flow path.

Exemplary Embodiment 7

Figure 21A:
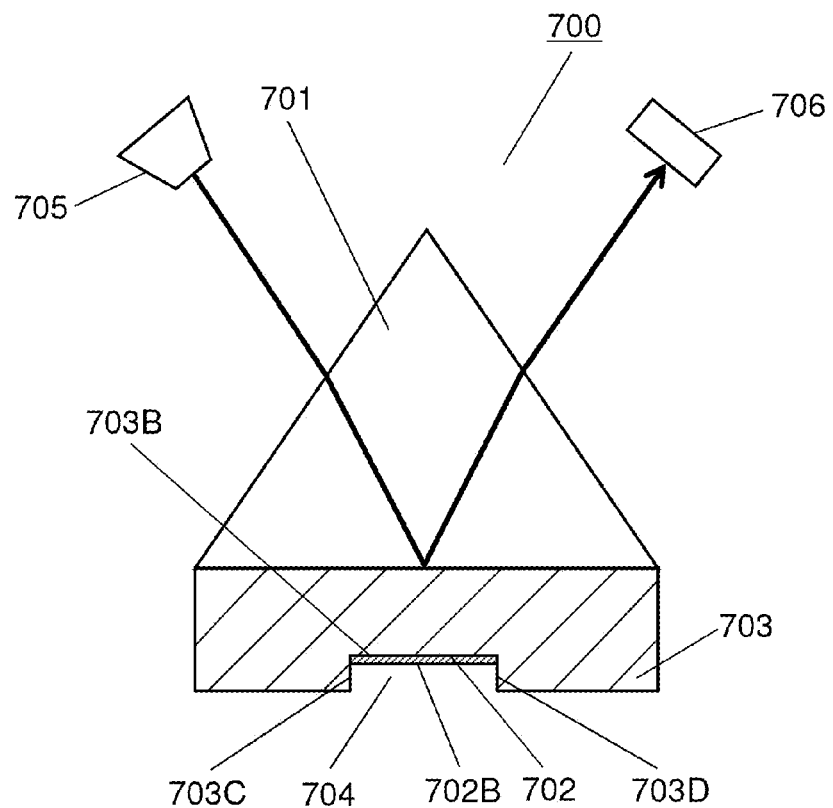
FIG. 21A is a sectional view of a sensor device in accordance with Exemplary Embodiment 7 of the present disclosure.
Figure 21B:
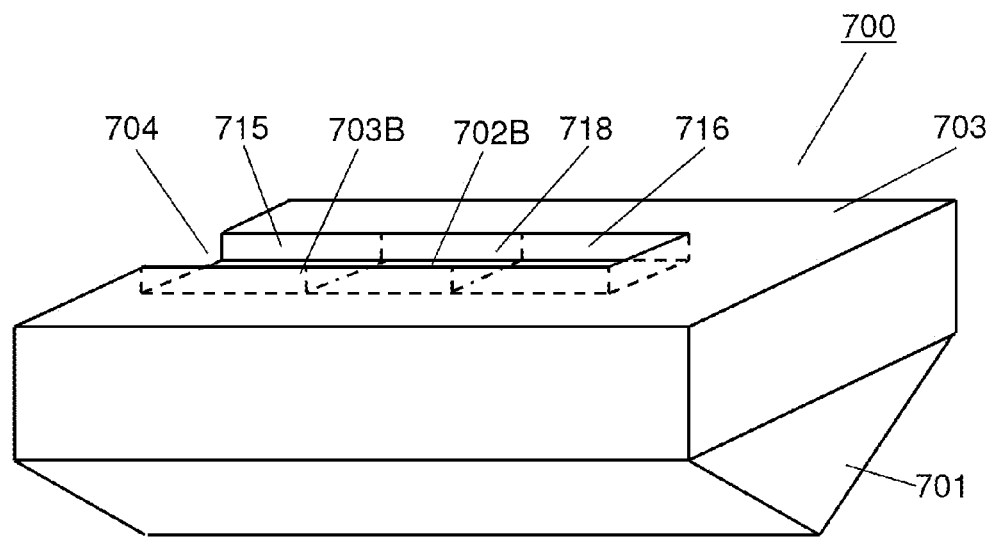
FIG. 21B is a bottom sectional view of the sensor device in accordance with Embodiment 7.

FIGS. 21A and 21B are a sectional view and a perspective bottom view of sensor device 700 in accordance with Exemplary Embodiment 7, respectively. Sensor device 700 is an attenuated total reflection (ATR) type sensor device.

Sensor device 700 includes prism 701, insulating layer 703 disposed on a lower surface of prism 701, and metal layer 702 disposed on a lower surface of insulating layer 703. Insulating layer 703 has a predetermined dielectric constant. The lower surface of insulating layer 703 is flat.

Insulating layer 703 of sensor device 700 is made of transparent insulating material, such as glass. Lower surface of insulating layer 703 has flow path 704 therein having a groove shape. Flow path 704 is constituted by three surfaces, side surface 703C, side surface 703D, and lower surface 702B of metal layer 702. Metal layer 702 is disposed on at least a part of lower surface 703B of insulating layer 703. Side surface 703C constitutes a first side surface of flow path 704. Side surface 703D constitutes a second surface of flow path 704. Lower surface 702B of metal layer 702 constitutes an upper surface of flow path 704.

Flow path 704 includes input region 715 configured to have a sample input thereto, discharge region 716 configured to have the sample discharged, and specific region 718 disposed between input region 715 and discharge region 716. The sample flows in region 718 functions as an aggregate trapping section for trapping aggregates containing analytes in the sample. Flow path 704 has carriers adsorbed physically therein. Each carrier has plural acceptors fixed on a surface thereof. The acceptors are specifically bound with the analytes to produce an aggregate. Sensor device 700 shown in FIG. 21A is actually used upside down.

The sample input into input region 715 flows toward discharge region 716 when a user squeezes out the sample with a pipette. The analytes in the sample are specifically bound with the carriers disposed in flow path 704, thereby forming the aggregates. The aggregates are trapped at region 718. Region 718 may be configured similarly to any one of specific regions 18, 118, 218, 318, 418, 518a, and 518b according to Embodiments 1, 2, 4, 5, and 6.

Surface plasmon wave (i.e. compression wave of electrons) is provided on an interface between metal layer 702 and insulating layer 703. Light source 705 is disposed above prism 701 and supplies P-polarized incident light to prism 701 under a condition of total reflection. This incident light causes an evanescent wave on both the surfaces of metal layer 702 and insulating layer 703. The light totally reflected on metal layer 702 is received by detector 706 which detects an intensity of the light.

When a wave-number matching condition in which a wave number of the evanescent wave matches wave number of the surface plasmon wave is satisfied, the light energy supplied from light source 705 is used for exciting the surface plasmon wave, so that the light intensity decreases. The wave-number matching condition depends on an incident angle of the light supplied from light source 705. Therefore, an intensity of reflected light is detected with detector 706 while the incident angle changes, and then, the intensity of the reflected light decreases at a certain incident angle.

A resonant angle at which the intensity of the reflected light takes a minimum value depends on the dielectric constant of insulating layer 703. A specific bound substance is produced by the acceptors and the analytes (i.e. an object to be measured in the sample) that are specifically bound together. When the specific bound substance is formed on the upper surface of insulating layer 703, the dielectric constant of layer 703 changes, and the resonant angle also changes accordingly. Upon the change of the resonant angle being monitored, a binding strength of the specific binding between the analytes and the acceptors or a speed of the specific binding can be detected.

In sensor device 700 in accordance with Embodiment 7, specific region 718 of flow path 704 traps the aggregates containing the analytes, so that the dielectric constant at region 718 may change more remarkably than other regions of flow path 704. Therefore, sensor device 700 has higher detection sensitivity to the analytes than conventional sensor device 600 shown in FIG. 22 which does not trap aggregates but allows the aggregates to distribute uniformly in a flow path thereof.

As described above, each sensor device according to the present disclosure traps the aggregates containing the acceptors at the specific region in the flow path, so that the acceptors can locally concentrate to the specific region. The dielectric constant of the specific region thus changes more remarkably than other regions, and the acceptors in the sample can be detected at a higher sensitivity.

In Embodiments 1 to 7, the metal layer refers to not only a sheet-like layer but also a layer covered with fine metal particles.

In the sensor devices shown in, e.g. FIGS. 2A, 4A, 4B, 8A, 8B, 9, and 11, the carriers and the acceptors are disposed only on lower surface 2B of metal layer 2; however, the structure is not limited to this. For instance, the carriers and the acceptors may be disposed only on upper surface 3A of metal layer 3, or disposed both on lower surface 2B and upper surface 3A of metal layers 2 and 3, providing the same effect.

In the embodiments, terms, such as "upper surface", "lower surface", "above", "below", indicating directions indicate relative directions depending on relative positional relations of structural elements, such as the flow path and the metal layers, of the sensor device, and do not indicate absolute directions, such as a vertical direction.

INDUSTRIAL APPLICABILITY

A sensor device according to the present disclosure has high detection sensitivity with a small and simple structure, so that it can be useful for small and inexpensive biosensors.

The invention claimed is:

1. A device for detecting analytes in a sample, comprising:
a sensor body including:
a flow path surrounded by an upper surface, a lower surface, a first side surface, and a second side surface which faces the first side surface, the upper surface of the flow path being configured to allow an incident electromagnetic wave supplied thereto, the flow path having an input region, a discharge region and an aggregate trapping section disposed between the input region and the discharge region;
a first metal layer disposed at least on a part of the upper surface of the flow path at the aggregate trapping section; and
a second metal layer disposed at least on a part of the lower surface of the flow path at the aggregate trapping section, the second metal layer facing the first metal layer; and
a plurality of carriers configured to flow with the sample in the flow path,
wherein each of the plurality of carriers has a plurality of acceptors fixed on a surface of the each of the plurality of carriers, the plurality of acceptors being specifically bound with the analytes for forming an aggregate when the sample contains the analytes, a diameter of the aggregate being larger than a diameter of each of plurality of carriers,
first acceptors among the plurality of acceptors are fixed to a first carrier among the plurality of carriers,
second acceptors among the plurality of acceptors are fixed to a second carrier among the plurality of carriers,
the aggregate includes the first carrier, the first acceptors, the second carrier, the second acceptors, and a first analyte among the analytes,
the first analyte is specifically bound with one of the first acceptors and specifically bonded with one of the second acceptors,
a distance between the upper surface and the lower surface of the aggregate trapping section is larger than the diameter of the aggregate,
a distance between the upper surface and the lower surface of the discharging region is larger than the diameter of each of the plurality of carriers and smaller than the diameter of the aggregate, and upon being trapped at the aggregate trapping section, the aggregate is detected by the electromagnetic wave, thereby detecting the analytes in the sample.

2. The device of claim 1, wherein the plurality of carriers are physically adsorbed and fixed in the flow path.

3. The device of claim 1,
wherein the flow path further includes a further region different from the aggregate trapping section, and
wherein a density of the plurality of carriers in the aggregate trapping section is larger than a density of the plurality of carriers in the further region.

4. The device of claim 1, wherein the plurality of acceptors are configured to be chemically adsorbed and fixed onto a surface of at least one of the first metal layer and the second metal layer in the aggregate trapping section of the flow path.

5. The device of claim 1,
wherein a distance between the first side surface and the second side surface of the flow path decreases from the input region toward the discharge region, and
wherein a distance between the first side surface and the second side surface in the discharge region is larger than the diameter of each of the plurality of carriers and smaller than the diameter of the aggregate.

6. The device of claim 1,
wherein the aggregate trapping section includes a plurality of pillars disposed in the flow path, and
wherein an interval between two pillars out of the pillars adjacent to each other is larger than the diameter of each of the plurality of carriers and smaller than the diameter of the aggregate.

7. The device of claim 1,
wherein the aggregate trapping section has a mesh structure disposed in the flow path, and
wherein a minimum value of aperture widths of the mesh structure is larger than the diameter of each of the plurality of carriers and smaller than the diameter of the aggregate.

8. The device of claim 7, wherein the mesh structure is made of fibrous substance of $SiO_2$ nano-fiber.

9. The device of claim 1, wherein distance D1 between the upper surface and the lower surface at the aggregate trapping section and distance D2 between the upper surface and the lower surface at the discharging region satisfy one of relations (a) and (b) with integers m1 and m2, a wavelength $\lambda$ of the electromagnetic wave in vacuum, a refraction index n in the flow path, and an incident angle $\theta$ of the electromagnetic wave:

$$(m1+\tfrac{1}{2})\times\lambda=2\times n\times D1\times\cos\theta, \text{ and } (m2+\tfrac{1}{2})\times\lambda=2\times n\times D2\times\cos\theta; \text{ and} \qquad (a)$$

$$m1\times\lambda=2\times n\times D1\times\cos\theta, \text{ and } m2\times\lambda=2\times n\times D2\times\cos\theta \qquad (b).$$

10. The device of claim 1,
wherein at least one of the first side surface and the second side surface meanders to form a recess, and
wherein the recess constitutes the aggregate trapping section.

11. The device of claim 1, further comprising an absorber disposed near the discharge region, the absorber being configured to absorb the sample.

12. The device of claim 1, further comprising an ultrasonic wave generator for applying an ultrasonic wave into the flow path.

13. The device of claim 1, further comprising a heat source for heating an inside of the flow path.

14. The device of claim 1,
wherein the plurality of carriers are made of magnetic material, and
wherein the flow path is configured to have a magnetic field applied thereto.

15. The device of claim 1, wherein the electro-magnetic wave is light containing a visible light band.

16. A device for detecting analytes in a sample, comprising:
a sensor body including:
a flow path surrounded by an upper surface, a lower surface, a first side surface, and a second side surface which faces the first side surface, the upper surface of the flow path being configured to allow an incident electromagnetic wave supplied thereto, the flow path having an input region, a discharge region and an aggregate trapping section disposed between the input region and the discharge region;
a first metal layer disposed at least on a part of the upper surface of the flow path at the aggregate trapping section; and
a second metal layer disposed at least on a part of the lower surface of the flow path at the aggregate trapping section, the second metal layer facing the first metal layer; and
a plurality of carriers configured to flow with the sample in the flow path, wherein:
each of the plurality of carriers has a plurality of acceptors fixed on a surface of the each of the plurality of carriers, the plurality of acceptors being specifically bound with the analytes for forming an aggregate when the sample contains the analytes, a diameter of the aggregate being larger than a diameter of each of plurality of carriers,
first acceptors among the plurality of acceptors are fixed to a first carrier among the plurality carriers,
second acceptors among the plurality of acceptors are fixed to a second carrier among the plurality of carriers,
the aggregate includes the first carrier, the first acceptors, the second carrier, the second acceptors, and a first analyte among the analytes,
the first analyte is specifically bound with one of the first acceptors and specifically bonded with one of the second acceptors,
the aggregate trapping section includes a plurality of pillars disposed in the flow path,
an interval between adjacent pillars is larger than the diameter of each of the plurality of carriers and smaller than the diameter of the aggregate, and
upon being trapped at the aggregate trapping section, the aggregate is detected by the electromagnetic wave, thereby detecting the analytes in the sample.

17. The device according to claim 16, wherein the interval between adjacent pillars is configured to prevent the aggregates from flowing into the discharge region and to pass the plurality of carriers through the trapping section and flow into the discharge region.

18. The device according to claim 1, wherein a distance between the upper surface and the lower surface of the discharging region is configured to prevent the aggregate from flowing into the discharge region.

19. A device for detecting analytes in a sample, comprising:
a sensor body including:
a flow path surrounded by an upper surface, a lower surface, a first side surface, and a second side surface which faces the first side surface, the upper surface of the flow path being configured to allow an incident electromagnetic wave supplied thereto, the flow path having an input region, a discharge region and an aggregate trapping section disposed between the input region and the discharge region;
a first metal layer disposed at least on a part of the upper surface of the flow path at the aggregate trapping section;
a second metal layer disposed at least on a part of the lower surface of the flow path at the aggregate trapping section, the second metal layer facing the first metal layer; and
a plurality of carriers configured to flow with the sample in the flow path, wherein: each of the plurality of carriers has a plurality of acceptors fixed on a surface of the each of the plurality of carriers, the plurality of acceptors being specifically bound with the analytes for forming an aggregate when the sample contains the analytes, a diameter of the aggregate being larger than a diameter of each of plurality of carriers,
first acceptors among the plurality of acceptors are fixed to a first carrier among the plurality carriers,
second acceptors among the plurality of acceptors are fixed to a second carrier among the plurality of carriers,
the aggregate includes the first carrier, the first acceptors, the second carrier, the second acceptors, and a first analyte among the analytes,
the first analyte is specifically bound with one of the first acceptors and specifically bonded with one of the second acceptors,
a distance between the upper surface and the lower surface of the aggregate trapping section is larger than twice the diameter of each of the plurality of carriers,
a distance between the upper surface and the lower surface of the discharging region is larger than the diameter of each of the plurality of carriers and smaller than twice the diameter of each of the plurality of carriers, and
upon being trapped at the aggregate trapping section, the aggregate is detected by the electromagnetic wave, thereby detecting the analytes in the sample.

20. The device according to claim 19, wherein the distance between the upper surface and the lower surface of the discharging region is configured to prevent the aggregate from flowing into the discharge region.

21. The device according to claim 1, wherein the carriers are made of a same material.

22. The device according to claim 1, wherein the aggregate further includes a second analyte among the analytes which is specifically bound with another one of the second acceptors.

23. The device according to claim 22, wherein:
third acceptors among the plurality of acceptors are fixed to a third carrier among the carriers,
the second analyte is specifically bound with one of the third acceptors, and
the aggregate further includes the third carriers and the third acceptors.

24. The device according to claim 16, wherein the carriers are made of a same material.

25. The device according to claim 16, wherein the aggregate further includes a second analyte among the analytes which is specifically bound with another one of the second acceptors.

26. The device according to claim 25, wherein:
third acceptors among the plurality of acceptors are fixed to a third carrier among the carriers, the second analyte is specifically bound with one of the third acceptors, and the aggregate further includes the third carriers and the third acceptors.

27. The device according to claim 19, wherein the carriers are made of a same material.

28. The device according to claim 19, wherein the aggregate further includes a second analyte among the analytes which is specifically bound with another one of the second acceptors.

29. The device according to claim 28, wherein:

third acceptors among the plurality of acceptors are fixed to a third carrier among the carriers, the second analyte is specifically bound with one of the third acceptors, and the aggregate further includes the third carriers and the third acceptors.

\* \* \* \* \*